United States Patent
Lohmeier et al.

(10) Patent No.: US 9,993,307 B2
(45) Date of Patent: Jun. 12, 2018

(54) ROBOTIC SURGERY SYSTEM AND SURGICAL INSTRUMENT

(71) Applicant: KUKA Laboratories GmbH, Augsburg (DE)

(72) Inventors: Sebastian Lohmeier, Munich (DE); Wolfgang Schober, Pottmes (DE)

(73) Assignee: KUKA Deutschland GmbH, Augsburg (DE)

( * ) Notice: Subject to any disclaimer, the term of this patent is extended or adjusted under 35 U.S.C. 154(b) by 584 days.

(21) Appl. No.: 14/523,713

(22) Filed: Oct. 24, 2014

(65) Prior Publication Data

US 2015/0105799 A1 Apr. 16, 2015

Related U.S. Application Data

(63) Continuation of application No. PCT/EP2013/001253, filed on Apr. 25, 2013.

(30) Foreign Application Priority Data

Apr. 27, 2012 (DE) .......................... 10 2012 008 537
Mar. 15, 2013 (DE) .......................... 10 2013 004 591

(51) Int. Cl.
*A61B 19/00* (2006.01)
*A61B 34/30* (2016.01)
(Continued)

(52) U.S. Cl.
CPC .............. *A61B 34/30* (2016.02); *A61B 34/71* (2016.02); *A61B 46/10* (2016.02);
(Continued)

(58) Field of Classification Search
CPC ......... A61B 34/30; A61B 34/71; A61B 46/10; A61B 2090/0813; A61B 2090/067; A61B 2017/00876; A61B 2017/00477
See application file for complete search history.

(56) References Cited

U.S. PATENT DOCUMENTS 5,814,038 A 9/1998 Jensen et al.
5,891,094 A 4/1999 Masterson et al.
(Continued)

FOREIGN PATENT DOCUMENTS

CN 2238619 A 10/1996
CN 101868191 A 10/2010
(Continued)

OTHER PUBLICATIONS

European Patent Office; Invitation to Pay Additional Fees in International Patent Application No. PCT/EP2013/001253 dated Jul. 23, 2013; 5 pages.

(Continued)

*Primary Examiner* — Julian W Woo
(74) *Attorney, Agent, or Firm* — Wood Herron & Evans LLP

(57) ABSTRACT

A robotic surgery system includes a robot and an instrument assembly. The instrument assembly includes a drive unit with at least one rotary drive having an electric motor and a drive shaft that has a coupling part for coupling to a drive shaft of the instrument; an instrument including an instrument shaft and a drive shaft that has a coupling part for coupling to a drive shaft of the drive unit; and an instrument interface including a sheath that encompasses the drive unit. In order to detachably couple an instrument module to an instrument part of a surgical instrument, an electromagnet in a magnet assembly of the instrument module is activated or deactivated, a permanent magnet of said magnet assembly is moved into a locking position and/or an angular position of a coupled counter element assembly of the instrument part is detected by an angle sensor of the instrument module.

18 Claims, 14 Drawing Sheets

(51) Int. Cl.
*A61B 34/00* (2016.01)
*A61B 46/10* (2016.01)
*B25J 19/00* (2006.01)
*G01D 5/54* (2006.01)
*A61B 17/00* (2006.01)
*A61B 90/00* (2016.01)

(52) U.S. Cl.
CPC ............ *B25J 19/0075* (2013.01); *G01D 5/54* (2013.01); *A61B 2017/00477* (2013.01); *A61B 2017/00876* (2013.01); *A61B 2090/067* (2016.02); *A61B 2090/0813* (2016.02)

(56) References Cited

U.S. PATENT DOCUMENTS

| | | | |
|---|---|---|---|
| 6,436,107 | B1 | 8/2002 | Wang et al. |
| 6,478,681 | B1 | 11/2002 | Overaker et al. |
| 6,607,475 | B2* | 8/2003 | Doyle .................... A61B 34/37 600/1 |
| 7,691,103 | B2* | 4/2010 | Fernandez ............. A61B 18/14 606/41 |
| 8,377,044 | B2* | 2/2013 | Coe .................. A61B 17/00234 606/1 |
| 8,998,058 | B2* | 4/2015 | Moore ................. A61B 17/072 227/175.2 |
| 9,743,995 | B2* | 8/2017 | Lohmeier .............. A61B 34/71 |
| 2004/0045557 | A1 | 3/2004 | Lee et al. |
| 2005/0228440 | A1 | 10/2005 | Brock et al. |
| 2007/0016174 | A1 | 1/2007 | Millman et al. |
| 2008/0015552 | A1* | 1/2008 | Doyle ................ A61B 17/1222 606/1 |
| 2008/0243106 | A1 | 10/2008 | Coe et al. |
| 2010/0079099 | A1 | 4/2010 | Katsuki et al. |
| 2010/0154578 | A1 | 6/2010 | Duval |
| 2011/0295270 | A1 | 12/2011 | Giordano et al. |
| 2012/0045598 | A1* | 2/2012 | Hagn .................... A61B 46/10 428/34.1 |

FOREIGN PATENT DOCUMENTS

| | | |
|---|---|---|
| CN | 102264307 A | 11/2011 |
| CN | 104363854 A | 2/2015 |
| DE | 10124490 A1 | 11/2002 |
| KR | 19990087101 A | 12/1999 |
| WO | 2009061915 A2 | 5/2009 |
| WO | 2010121117 A1 | 10/2010 |
| WO | 2010127940 A1 | 11/2010 |

OTHER PUBLICATIONS

European Patent Office; Search Report and Written Opinion in International Patent Application No. PCT/EP2013/001253 dated Oct. 4, 2013; 20 pages.
German Patent Office; Examination Report in German Patent Application No. 10 2013 004 591.6 dated Dec. 16, 2013; 5 pages.
German Patent Office; Examination Report in German Patent Application No. 10 2012 008 537.0 dated Nov. 14, 2012; 5 pages.
U.S. Patent and Trademark Office; Office Action in U.S. Appl. No. 14/523,633 dated Jun. 16, 2016; 20 pages.
Chinese Patent Office; Office Action in Chinese Patent Application No. 201510012306.3 dated Dec. 6, 2016; 14 pages.
Chinese Patent Office; Office Action in Chinese Patent Application No. 201510010028.8 dated Jan. 11, 2017; 28 pages.
Chinese Patent Office; Office Action in Chinese Patent Application No. 201510012294.4 dated Apr. 5, 2016; 11 pages.
Korean Patent Office; Decision for Grant of Patent in Korean Patent Application No. 2014-7032819 dated Sep. 28, 2016; 3 pages.
U.S. Patent Office; Office Action in U.S. Appl. No. 14/523,693 dated Sep. 28, 2016; 29 pages.
Chinese Patent Office; Office Action in Chinese Patent Application No. 201380031705.3 dated Dec. 1, 2016; 11 pages.
Korean Patent Office; Office Action in Korean Patent Application No. 2014-7032817 dated May 31, 2016; 10 pages.
Chinese Patent Office; Office Action in Chinese Patent Application No. 201510010028.8 dated Jan. 17, 2018; 18 pages.

* cited by examiner

Fig. 22
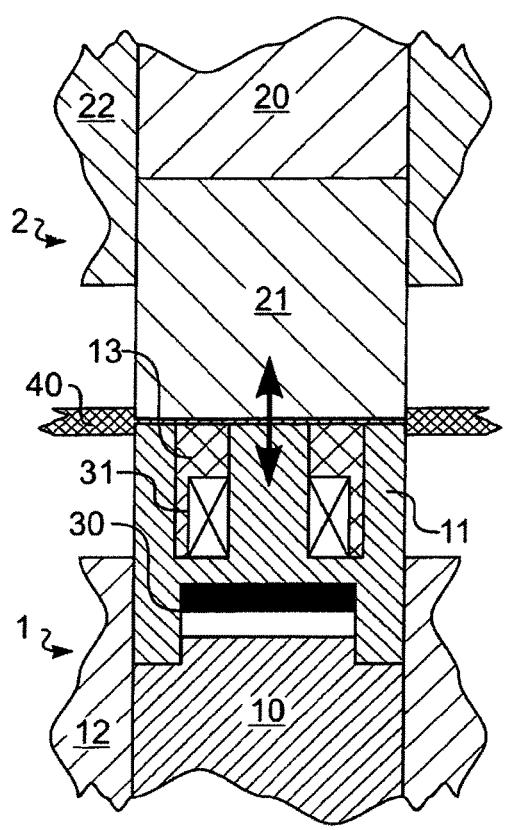
Fig. 23
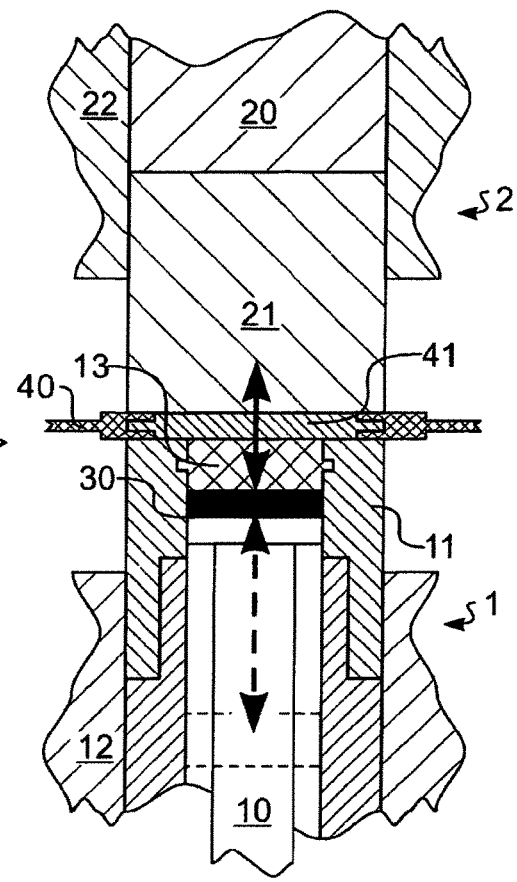
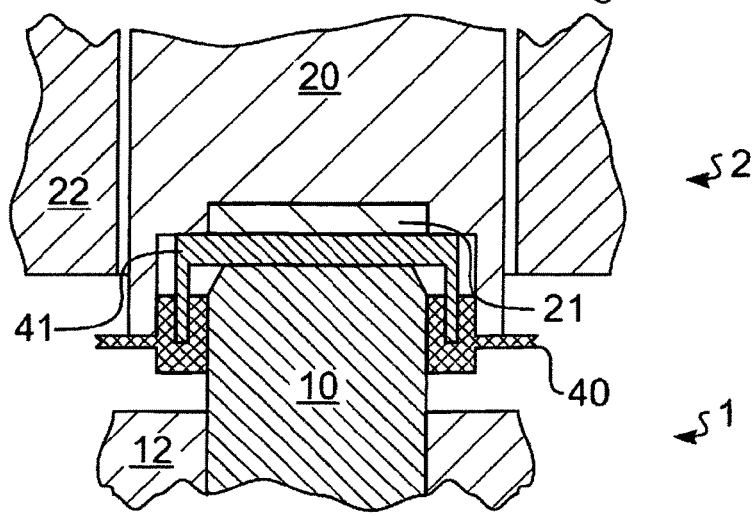
Fig. 24

ROBOTIC SURGERY SYSTEM AND SURGICAL INSTRUMENT

CROSS-REFERENCE

This application is a continuation of International Patent Application No. PCT/EP2013/001253, filed Apr. 25, 2013 (pending), which claims priority to DE 10 2012 008 537.0 filed Apr. 27, 2012, and DE 10 2013 004 591.6 filed Mar. 15, 2013; and is related to U.S. patent application Ser. No. 14/523,633 (now abandoned), U.S. patent application Ser. No. 14/523,693 (now U.S. Pat. No. 9,743,995), and U.S. patent application Ser. No. 14/523,742 (pending), each filed Oct. 24, 2014, the disclosures of which are incorporated by reference herein in their entirety.

TECHNICAL FIELD

The present invention relates to a robotic surgery system with a robot and an instrument assembly fastened thereat, such an instrument assembly comprising a drive unit, an instrument, and an instrument interface. The invention also relates to a drive unit, an instrument, and an instrument interface for an instrument assembly, as well as a cover for the instrument interface, and a method for their application.

BACKGROUND

Surgical instruments should be as sterile as possible. On the other hand, robots are hard to sterilize, for example due to lubricants, abrasions, and the like.

Accordingly, a robot with an adapter socket is known from WO 2009/061915 A2, with an adapter of a sterile cover being fastened thereat which encompasses the robot. An instrument is fastened at the sterile side, facing away from the robot, with its end effector being actuated by pulleys inside the instrument shaft.

For this purpose, disks which are rotationally supported side-by-side in the sterile adapter are coupled to counter disks, which are integrated in the robot arm. The rotary drives for actuating the counter disks are arranged in the robot base; the drive moments are transmitted via pulleys into the robot arm, so that the instrument, not having a drive of its own, can easily be manipulated.

SUMMARY

One objective of an aspect of the present invention is to provide an improved robotic surgery system.

Another aspect of the present invention relates to a surgical instrument, in particular a robot-guided one, comprising an instrument part, in particular an instrument shaft with an end effector, as well as an instrument module that can be coupled thereto in a detachable fashion, in particular a drive module for actuating the end effector, as well as a method for coupling such an instrument part.

In minimally invasive surgery, a surgical instrument is guided through a local opening into a patient. In particular when the instrument is guided by a robot, an end effector, for example a pair of scissors or an endoscopic optic, can be actuated inside the patient by an extracorporeal drive, for example an electric motor, for example pivoted and/or closed. In particular for the use of different end effectors and/or in order to allow better fulfillment of the requirements for sterility during surgery, it is advantageous for the drive and the end effector to be detachable from each other.

A surgical instrument with a drive module and an instrument shaft is known from WO 2009/061915 A2. Rotary coupling elements of the drive module and rotational counter elements of the instrument shaft aligned thereto are coupled via sterile couplings in a form-fitting fashion, achieving an excellent alignment.

One objective of an aspect of the present invention is to improve the coupling of an instrument part to an instrument module of a surgical instrument, in particular a robot-guided one.

Robotic Surgery System

A robotic surgery system according to one aspect of the present invention comprises one or more robots. In one embodiment, a robot may have six or more joints, in particular swivel joints, with more than six joints being able to allow an advantageous positioning of the redundant robot. In one embodiment, the robot or robots have a control. Here, several robots may have a common central control or individual controls, which for a more compact illustration are also called jointly a control of the robots. In one embodiment a robot may be arranged at a surgery table, in particular in a detachable fashion.

One instrument assembly is fastened respectively at one or more robots of the robotic surgery system according to one of the aspects of the present invention explained in the following. In one embodiment an instrument assembly is fastened in a detachable fashion at a robot, in particular in a form-fitting fashion, in a friction-fitting fashion, and/or magnetically, in particular electro-magnetically. In one embodiment the instrument assembly, in particular a drive unit of the instrument assembly, comprises a housing, which is fastened at an exterior of the robot, in particular a robotic (end or tool) flange, respectively, for example by way of a screwed, latched, or clamping connection. Additionally or alternatively, an instrument interface and/or an instrument of the instrument assembly may be arranged in particular at the exterior of the robot, in particular at a robot (end or tool) flange, respectively.

Instrument Assembly

An instrument assembly according to one aspect of the present invention is implemented accordingly for the fastening at a robot and/or embodied as a robot-guided instrument assembly. It comprises a drive unit, an instrument, and an instrument interface according to one of the aspects of the present invention explained in the following.

By the instrument assembly itself being equipped with a drive unit, preferably embodied overall in a mobile fashion, a transmission of drive forces from the robot itself to the instrument can be advantageously omitted, thus the robot can be designed with smaller dimensions, which in particular can allow the cooperation of several slim robots within a limited operating space. Additionally, the drive unit can advantageously be adjusted easily to different instruments or exchanged as well. It is preferably embodied as an independent module and/or one independent from the robot.

In one embodiment the instrument assembly comprises two or more different drive units and/or two or more different instruments, which optionally can be connected like modules with an instrument and/or a drive unit to an instrument assembly fastened at the robot. Different drive units and/or instruments may in particular differ by the number and/or capacity of actuated degrees of freedom. For example, a drive unit with three actuated degrees of freedom may optionally be connected to an instrument with one or two actuated degrees of freedom and two and/or one not-actuated one, i.e. unused and/or blind degree of freedom, and to instruments with three actuated degrees of freedom, which have different end effectors.

The instrument and the drive unit are connected to each other in a detachable fashion, with an instrument interface being arranged between the drive unit and the instrument. The instrument and the drive unit may be fastened in particular in a form-fitting, friction-fitting, material-to-material, and/or magnetic fashion, preferably an electromagnetic one, to each other and/or to an instrument interface arranged between them. In particular, the instrument interface can be screwed, latched, clamped, or also adhered to the drive unit and/or the instrument, with the adhesion site being embodied as a predetermined separation point. Additionally or alternatively the drive unit may be screwed, latched, or clamped to the instrument. In one embodiment the instrument interface comprises an inherently stable flange for fastening the drive unit and/or the instrument. In one embodiment the drive unit is arranged at a proximal end and/or one distanced from the end-effector.

Drive Unit

A drive unit according to one aspect of the present invention comprises one or more, in particular three or four rotary drives with respectively at least one drive shaft each. In one embodiment one or more rotary drives of the drive unit comprise respectively one or more electric motors each, in particular direct current or alternating current motors, having a stator and a rotor. Additionally or alternatively one or more rotary drives of the drive unit may have one or more hydraulic motors and/or Piezo-drives each, which respectively move drive shaft(s) and/or can apply a torque thereupon. The drive shaft can in particular represent a rotor and/or runner of an electric and/or hydraulic motor. In one embodiment the rotary drive comprises a rotary drive, preferably a coaxial transmission, in particular an epicyclic gear, preferably a planetary gear or a harmonic-drive transmission, with the drive shaft representing a driven and/or output shaft of the transmission. In another embodiment a rotary drive is embodied as a direct drive. In the present invention it is in particular understood that the drive shaft is directly impinged by an in particular hydraulically, electrically, and/or (electro)magnetically generated drive moment without any interposed transmission. In particular, such a direct drive can be designed without any independent self-inhibition in one embodiment. This way, advantageously the instrument with the drive unit flange connected thereto can be removed from the patient. Additionally or alternatively a rotary drive may comprise a sensor, in particular a coaxial one, in particular a rotation and/or torque sensor arranged at the driving and/or the driven side.

The drive shaft comprises a coupling part for coupling to a drive shaft of the instrument, which is connected in a torque-proof fashion to the drive shaft. In one embodiment it may be designed axially-fixed to the drive shaft, in particular integrated with this. In another embodiment the coupling part is arranged in an axially displaceable fashion at the drive shaft, in particular in a form-fitting fashion, in particular via a fitting key, a helical gearing, a geared or polygonal shaft profile or the like. In one further development the coupling part is axially pre-stressed, in particular by means of a spring, against the instrument interface fastened at the drive unit or the instrument fastened at the drive unit. This way, in particular any axial play can be compensated and/or a compression force can be generated for a friction-fitting connection.

In one embodiment, one or more drive shafts are embodied as hollow shafts. In one embodiment the drive unit includes one or more drive shafts, each arranged concentrically and/or coaxially inside a hollow drive shaft surrounding it, in particular supported by it. Here, for a more compact illustration, the drive shaft which is arranged inside another drive shaft is respectively called the inner drive shaft, the other drive shaft is called the outer drive shaft. For example, if in one embodiment the drive unit comprises three drive shafts, here the innermost drive shaft, which may also be embodied as the hollow drive shaft, an inner drive shaft, a central drive shaft surrounding it, an outer drive shaft, and simultaneously another inner drive shaft, the outermost drive shaft surrounding it, another drive shaft. Simultaneously the drive unit may also include four or more concentric hollow drive shafts.

In one embodiment one or more rotary drives are arranged coaxially in reference to their respective drive shaft, in particular in reference to a common rotary axis of coaxial drive shafts. In particular, one or more rotary drives may be arranged aligned behind each other. Similarly, one or more rotary drives may be arranged parallel and offset in the radial and/or the circumferential direction in reference to their drive shafts, in particular in reference to a common rotary axis of coaxial drive shafts, and coupled therewith in particular via a spur gear or friction transmission. Simultaneously one or more rotary drives may be arranged at an angle, in particular a right angle, in reference to their respective drive shaft, in particular a common rotary axis of coaxial drive shafts, and coupled therewith in particular via a worm, helical, or crown-gear transmission.

A drive unit may respectively be connected wirelessly or in a wired fashion to an energy source and/or the controls. In one embodiment the cover of the instrument interface explained in the following encompasses, at least partially, also an energy and/or signal line of the drive unit.

Instrument

An instrument according to one aspect of the present invention comprises an instrument shaft, with an end effector comprising one or more parts potentially being arranged at its distal end and/or the end facing away from the drive unit, in particular a scalpel, a pair of pliers and/or legs of scissors, or the like.

In one embodiment the instrument represents an endosurgical and/or minimally invasive surgical instrument ("MIC"), in particular an endoscopic one, such as a laparoscopic or thoracoscopic one. In particular, the instrument shaft may be provided and/or embodied for the purpose to be inserted into the patient through an access, which is in particular equivalent essentially to the exterior diameter of the instrument shaft, in particular via a trocar, and actuated there.

The end effector may have one or more degrees of freedom. In particular one or more parts of the end effector may have one or two degrees of rotary freedom about an axis of rotation each, which are preferably aligned perpendicularly in reference to the axis of the shaft. For example, a two-part end effector may represent a pair of pliers and/or scissors, with their legs pivoting about the same rotary axis in opposite directions.

In order to actuate the end effector, the instrument comprises one or more drive shafts, in particular a drive shaft for actuating every degree of freedom, in one embodiment therefore in particular one, two, or three drive shafts.

The drive shaft comprises a coupling part for coupling to a drive shaft of the drive unit, which is torque-proof in reference to the drive shaft. In one embodiment it may be designed axially fixed with the drive shaft, in particular integrated therewith. In another embodiment the coupling part is arranged axially displaceably at the drive shaft, in particular in a form-fitting fashion, for example via a fitted key, a helical gearing, a toothed or polygonal shaft profile, or the like. In a further development the coupling part is axially pre-stressed, in particular by spring means, against the instrument interface fastened at the instrument or the drive unit fastened at the instrument.

In one embodiment one or more drive shafts are embodied as hollow shafts. In one embodiment the drive unit comprises one or more drive shafts, which are respectively arranged concentrically and/or coaxially inside a driving hollow shaft surrounding it, in particular supporting it.

By the (innermost) drive shaft of the instrument being embodied as a driving hollow shaft, in one embodiment the insertion and/or passage of an auxiliary instrument is advantageously enabled.

In one embodiment drive shafts of the drive unit and the instrument, coupled to each other, are aligned to each other. In one embodiment the drive shaft(s) is/are coaxially arranged in particular aligned or offset parallel in reference to the instrument shaft. This way, in one embodiment a radially compact design can be achieved. In another embodiment the drive shaft(s) is/are arranged in an angular fashion, in particular perpendicularly in reference to the instrument shaft. This way, in one embodiment the drive unit can be arranged in an angular fashion, in particular perpendicularly in reference to the instrument shaft.

In one embodiment the instrument comprises a transmission at the instrument side for converting a rotation of one or more drive shafts into a respective translation of one or more tensile and/or thrust means. A tensile means may in particular comprise one or more, in particular opposite rope, belt, or tape drums, a tensile and/or thrust means, one or more tensile and/or thrust rods, in particular opposite ones.

In one embodiment the transmission comprises respectively one guide bar, in particular for one or more drive shafts of the drive unit each. According to one embodiment, a guide bar comprises a sliding sheath, which is supported torque-proof in reference to the instrument shaft and is axially displaceable, in particular at the instrument shaft or a surrounding hollow drive shaft. A guide bar and/or groove is embodied in one sliding sheath and the drive shaft, inclined in particular in reference to the axial direction, in which a fitting element, in particular a feather key, is guided in a form-fitting fashion by the other sliding sheath and the drive shaft. This way a rotation of the drive shaft is converted into an axial translation of the sliding sheath, which this way can in particular actuate a tensile and/or thrust means.

When in one embodiment a drive shaft is supported in a hollow drive shaft, in a further development a sliding sheath of a guide bar coupled to a drive shaft can simultaneously form a radial bearing, in particular a movable bearing, between it and an adjacent drive shaft. A fixed bearing of a drive shaft is preferably arranged at an end of the instrument shaft facing the drive unit and/or at the proximal end.

In one embodiment the transmission is arranged in one half of the instrument shaft facing the drive unit and/or the proximal side. In another embodiment the transmission is arranged in one half of the instrument shaft facing away from the drive unit and/or the distal side. This way, the actuation can be advantageously transmitted over a large area of the instrument shaft by the tensile and/or thrust means and/or by the drive shafts.

Auxiliary Instrument

According to one aspect of the present invention, an instrument assembly comprises an auxiliary instrument, which, in particular in a detachable fashion, can be guided into and/or through the instrument of the instrument assembly, in particular a guiding tube of the instrument, in particular with a radial play or with a radial fitting. For this purpose, in one embodiment the auxiliary instrument is designed in a tubular fashion and may be stiff or flexible. According to one embodiment the instrument may have a guiding tube, in particular a stiff one, in particular a central one, in which the instrument shaft is arranged and/or in which it can extend, at least essentially, over the entire interior length of the instrument shaft. In a further development an (innermost) hollow drive shaft of the instrument may act as the guiding tube and/or form a guiding tube.

In one embodiment the auxiliary instrument may be embodied as a guide for gaseous and/or liquid media, in particular as a suction and/or supply passage, and/or as an electric and/or light-wave conductor, in order to conduct for example rinsing or surgical water-jet media to be drained and/or supplied in particular at a vacuum or pressure, conduct laser and/or illuminating light and/or power into the patient, and/or to guide optic and/or electric signals out of said patient.

In one embodiment the auxiliary instrument may be inserted through the instrument at a side of the instrument interface pointing away from the drive unit, so that it is advantageously not necessary to isolate it from the drive unit in a sterile fashion. In another embodiment the auxiliary instrument is inserted through the drive unit, in particular an (innermost) hollow drive shaft of the drive unit.

In addition to the auxiliary instrument or alternatively thereto, a drive means for an actuation of an end effector may be inserted, in particular in a detachable fashion, through the instrument of the instrument assembly, in particular an (innermost) hollow drive shaft of the instrument, in particular inserted with a radial play or a radial fitting. For this purpose, in one embodiment the drive means may be embodied in a tubular fashion and be stiff or flexible. The drive means may in particular have one or more tensile and/or thrust means and/or one or more rotary shafts.

Instrument Interface

An instrument interface according to one aspect of the present invention comprises a drive unit, in particular a cover encompassing it in a hermetically and/or sterile fashion. In one embodiment the cover is flexible, in particular like a film. In one embodiment the cover is sterile or can be sterilized at the exterior side facing way from the drive unit.

This way, the drive unit, which due to abrasion, lubricants, temperature, and/or moisture-sensitive components or the like can only be sterilized with difficulty, can be isolated from the surgery environment in a sterile fashion, with the actuation being transmitted through and/or via the interface into the instrument, which advantageously also can be sterilized.

In one embodiment, coupling parts of one or more drive shafts of the drive unit and corresponding, in particular coaxial drive shafts of the instrument are coupled to each other in a magnetic fashion. In particular in this case the instrument interface can be formed by a simple film, with preferably an air gap being formed between the coupling parts, coupled to each other in a magnetic fashion.

In one embodiment the instrument interface comprises one or more rotary intermediate elements, which are implemented to be coupled to one coupling part of a drive shaft of the drive unit and one coupling part of a drive shaft of the instrument each, in particular in a friction-fitting or form-fitting fashion, when the interface is arranged between the drive unit and the instrument, in particular fastened at the drive unit and/or the instrument.

The assembly of the intermediate elements is preferably equivalent to the assembly of the drive shafts and/or their coupling parts. Thus, if in one embodiment the drive shafts of the drive unit and/or the instrument are concentric, in particular the intermediate elements are also arranged concentrically in reference to each other, with preferably, as explained above, respectively one inner intermediate element, in particular an annular one, is arranged concentrically in an outer annular intermediate element, in particular supported here. In one further development the intermediate elements are supported in a sealing fashion, for example by bearing rings, which include labyrinth seals or the like. Sealed is understood in the present case in particular as sterile in the medical sense, in particular sealed such that solid, preferably also liquid, in particular also gaseous elements of a predetermined size can overcome the seal at the most in a predetermined maximum quantity and/or rate, which may also tend towards zero.

The instrument interface may have an inherently stable flange for fastening the drive unit and/or the instrument, in which the intermediate elements are rotationally supported, in particular in a sealed fashion.

Intermediate elements and coupling parts of the drive unit and/or the instrument may have contact surfaces for a friction-fitting coupling, which contact each other when the instrument interface is arranged between the drive unit and the instrument, and the instrument and the drive unit are directly connected and/or connected via the instrument interface. For a form-fitting coupling, such contact surfaces may include projections and recesses engaging each other and/or complementary steps. In particular, one or more projections and/or steps may be arranged at a coupling part and the intermediate part, which engage in a form-fitting fashion the recesses and/or complementary steps in the respectively other coupling part and intermediate element, when the instrument interface, in particular an inherently stable flange of the instrument interface, is arranged at the drive unit and/or the instrument.

Preferably the coupling part and the intermediate element may include spur gearing, in particular Hirth-gearing engaging each other.

In one embodiment the friction-fitting or form-fitting contact areas may be designed conically. This way, advantageously a self-centering and/or in particular in a combination with axially displaceable, preferably pre-stressed coupling parts, a compensation of an axial tolerance can be yielded.

In one embodiment the cover comprises an inner passage for an auxiliary instrument inserted through the instrument and the drive unit of the instrument assembly. This inner passage may be embodied in a tubular fashion and pass an inner(most) hollow drive shaft of the drive unit. In a further development it is sealed, in particular connected in a rotary fashion to an inner(most) intermediate element of the instrument interface coupled to the hollow drive shaft.

In a further development the inner passage comprises a blind plug and a cap ring. In an initial and/or assembly state the blind plug is fastened at one end of the inner passage, closes it, and covers a circumferential section of the inner passage. The blind plug can then be pulled through the drive unit so that it projects from an outlet opening of the cover and can be removed. Subsequently the cap ring can be fastened at the circumferential section of the inner passage, which is released by removing the blind plug, and additionally closes the outlet opening of the cover. This way, a torus-shaped cover can be provided with a sterile exterior surface, with the drive unit being arranged in its annular space and being isolated in a sterile fashion from the surgery environment, and with the openings of its passage being available for inserting the auxiliary instrument.

The above-described further development is in particular suitable for the above-explained drive unit with a hollow drive shaft. It can also be used for covering a robot with a tool flange comprising a hollow shaft, in particular in a sterile fashion. A (sterile) covering is in particular understood in the present case as a partially or entirely closed and/or closed at all sides, in particular hermetically, covering and/or encompassing.

According to one aspect of the present invention the cover, which may include in particular one or more features of the above-described cover of the instrument interface, therefore comprises generally a tubular inner passage for guiding a robot or an above-described drive unit through the hollow shaft and through an outlet opening of the cover, with the inner passage comprising a blind plug and a cap ring, comprising one or more parts, for fastening at the outlet opening and a in particular exterior circumferential and/or jacket area of the inner passage, which is released by removing the blind plug. The inner passage may in particular be supported rotationally at the cover or be embodied integrally therewith. It may in particular be embodied stiffly or flexibly. For a more compact illustration even a stiff tubular inner passage is generally characterized as tubular.

For encompassing the robot or the drive unit, initially the inner passage provided with the blind plug is guided through the hollow shaft and the outlet opening of the cover. The blind plug, which preferably has a closed exterior face and/or a tubular jacket, prevents any soiling of the interior of the tubular inner passage and the circumferential area of the inner passage covered by it. Similarly, the inner passage may initially be closed at its face, with the closed section subsequently being severed. In order to facilitate the passage the blind plug may include a stiff and/or flexible insertion aid, in particular a string or a rod.

Subsequently the blind plug is removed and the cap ring is fastened at the circumferential section of the inner passage, which was released by the removal of the blind plug. As described above, the cap ring, which may be embodied stiffly or flexibly, in a further development can be fastened at the outlet opening of the cover and close it, except for the inner passage. A part of the cap ring fastened at the circumferential section of the inner passage may be supported, in particular in a rotary fashion, at one part of the cap ring fastened at the outlet opening of the cover or be embodied integrally therewith and/or in one piece therewith.

The circumferential section of the inner passage, which was released by the removal of the blind plug, was protected by the blind plug from soiling during the insertion process. A fastening at the circumferential section is in particular understood in the present case as a fastening such that the circumferential section is covered partially or entirely by the cap ring, seen in the longitudinal direction of the inner passage. The circumferential section, which was released by the removal of the blind plug, may project beyond the cap ring in the longitudinal direction at one or both sides. Similarly, except for the circumferential section which was released by the removal of the blind plug or also a part of this circumferential section, the cap ring may also cover a circumferential section of the inner passage which previously was not covered by the cap ring.

According to one aspect of the present invention, a surgical instrument comprises an instrument module and an instrument that can be detachably connected thereto, in particular a connected one. The surgical instrument may in particular be robot-guided and/or the instrument module or the instrument part may have an in particular electro-mechanic interface for an in particular mechanical and/or signal-technological fastening at a robot. According to one aspect, a robot is protected with a robot-guided surgical instrument. In one embodiment the surgical instrument is a minimally-invasive instrument, which is provided and/or embodied for the partial insertion into a patient through a so-called trocar opening.

In one embodiment the instrument module comprises an instrument shaft that can be inserted into the patient with an end effector, with the instrument part, that can be connected thereto in a detachable fashion, comprising a drive for actuating the end effector. Simultaneously, the instrument module may also include a drive for actuating an end effector of an instrument shaft of the instrument part that can be inserted into a patient. For a more compact illustration, in the present case generally an instrument module and instrument part is being discussed which may respectively be embodied as a drive module and/or an end effector module and/or an end effector part.

The end effector may in particular represent a scalpel, a probe, scissors, pliers, or a clamp, an optic for transmitting and/or receiving electro-magnetic radiation and/or a fluid opening for inserting and/or suctioning out gas and/or liquids. An actuation of the end effector may in particular include the pivoting of the end effector about one, two, or three axes in reference to the instrument shaft and/or representing an actuation, in particular an opening and/or closing of the end effector. The drive may also include one or more electric motors. Additionally or alternatively the drive may also include one or more manual elements, in particular handles and/or wheels, for a manual actuation of the end effector. In general the drive may be implemented for an electromotive, electromagnetic, pneumatic, hydraulic, and/or manual actuation of the end effector.

In order to transmit a motion and/or force between the drive and the end effector, with an anti-parallel pair of forces (e.g. a torque) perhaps generally representing any force in the sense of the present invention, the instrument module includes a coupling element assembly with one or more coupling elements, the instrument part that can be connected thereto in a detachable fashion comprising a counter element assembly with one or more counter elements for coupling the coupling element assembly.

In one embodiment, one or more coupling elements and the counter element or elements that are or can be coupled thereto are be actuated in a translational, mobile fashion, respectively by a degree of freedom of the end effector. In particular, such coupling elements can be guided in a displaceable fashion in a slide-bearing of the instrument module, preferably in a torque-proof fashion, in particular embodied as a tappet. Additionally or alternatively, one or more coupling elements and the counter element or elements that can be or is/are coupled thereto are be rotationally mobile in order to respectively actuate a degree of freedom of the end effector. In particular, such coupling elements may be rotationally guided in a rotary bearing of the instrument module, in particular in an axially fixed fashion, in particular embodied as a shaft.

According to one aspect of the present invention, one or more, in particular all coupling elements of the coupling element assembly, can be or are magnetically coupled to the counter element assembly and/or its counter element(s). For this purpose, in one embodiment the coupling element or elements of the coupling element assembly of the instrument module each includes a magnetic assembly for the magnetic coupling of the counter element of the counter element assembly. The counter element or elements of the instrument part comprise(s) in one embodiment accordingly a section that can be magnetically impinged. A section that can be magnetically impinged is understood in particular as a section comprising a material which has a permeability value and/or a relative permeability $\mu_r$, which amounts to at least 10, in particular a section comprising a ferromagnetic or permanently magnetic material.

Via the magnetic coupling of the coupling assembly and counter element assembly, the drive can advantageously be effectively and detachably connected to the end effector, in particular in a simple, sterile, and/or reliable fashion. Here, in one embodiment the magnetic assembly can be arranged at the driving side and/or the instrument module may be embodied as a drive module. This way, in particular the instrument part with the instrument shaft and/or the end effector can be embodied easier, more compact, and/or cheaper, in particular as a disposable article, and/or have or obtain better abilities for sterilization. Simultaneously, the magnetic assembly may also be arranged at the side of the end effector and/or the instrument module may comprise the instrument shaft and the end effector.

In one embodiment the magnetic assembly of one or more coupling elements may include one or more permanent and/or long-lasting magnets.

In one embodiment the permanent magnet or magnets is/are sized magnetically such that they securely couple the respective counter element when it is adjacent to said coupling element; however, by an appropriately greater disassembly force it/they can be decoupled therefrom, in particular by way of distancing the coupling and the counter element from each other.

Preferably, however, one coupling and one counter element may be decoupled from each other without being distanced from each other.

For this purpose the magnetic assembly of one or more coupling elements comprises in one embodiment one or more electric magnets, which can be and/or is/are optionally electrified, in particular by a control means embodied for this purpose, which can be in particular implemented in a drive control of the instrument.

By an optionally electrified electromagnet, in one embodiment a currentless opened coupling between the coupling element and the counter element and/or a so-called noncurrent principle may be provided. This can preferably allow the instrument module and/or the instrument part and/or the drive and the end effector to become currentless and thus be separated reliably in order to allow manually removing the end effector out of the patient, even in case of a defect.

Simultaneously, in one embodiment a currentless closed coupling may be provided between the coupling element and the counter element and/or a so-called operating current principle by an optionally electrified electro magnet. This may preferably allow to also reliably couple the instrument module and the instrument part and/or the drive and the end effector, even in case of a power outage.

In one embodiment a magnetic assembly is provided for this purpose with one or more optionally electrified electromagnets as well as one or more permanent magnets opposite thereto. A permanent magnet opposite the electromagnet is understood in the present case in particular as a permanent magnet whose magnetic field is weakened by the electrified electromagnet in the coupling area of the coupling element and the counter element, in particular at least essentially compensated and/or neutralized. If this weakening and/or compensation is omitted for non-electrified electromagnets, the then un-weakened and/or uncompensated permanent magnet couples the coupling element and the counter element.

In one embodiment additionally or alternatively a magnetic assembly may have both one or more optionally electrified electromagnets as well as one or more permanent magnets operating in the same direction. In the present case, a permanent magnet operating in the same direction as an electromagnet is understood as a permanent magnet whose magnetic field is amplified by the electrified electromagnet in a coupling section of the coupling element and the counter element. This way, the adhesion force can be advantageously increased. In reference to a solution without a permanent magnet, in one embodiment the electromagnetic flux required for transmitting force and thus the energy consumption and the generation of heat can be reduced. In reference to a solution without an electromagnet, in one embodiment the permanent magnet may be reduced. Additionally or alternatively, in one embodiment one or more permanent magnets of a magnetic assembly can be arranged at, particularly in, the coupling element, adjustably between a locked and an unlocked position different therefrom, in particular supported in a displaceable and/or rotational fashion, and/or can be adjusted, in particular shifted and/or displaced. In a further development the permanent magnet or magnets are adjustable in an electromotive, hydraulic, pneumatic, and/or manual fashion. Additionally or alternatively the permanent magnet or magnets may be lockable in the locked, the unlocked, and/or in a position different from these two positions.

By removing a permanent magnet from the coupling area of the coupling element and the counter element, in one embodiment the magnetic coupling of the coupling element and the counter element can be reduced by this permanent magnet, and this way the coupling element and the counter element can be decoupled. Additionally or alternatively, in one embodiment the coupling element may include a magnetically conductive section for coupling the counter element, which is magnetically impinged by a permanent magnet, at least essentially, only when it is in the locked position and/or when it is magnetically separated from the permanent magnet when it is in the unlocked position.

In general, in one embodiment the coupling element may comprise a magnetically conductive section for coupling the counter element, which in particular optionally, preferably by way of electrifying and/or non-electrifying at least one electromagnet and/or adjusting at least one permanent magnet can be brought into the locked position, by which the magnetic arrangement can be and/or is impinged magnetically. A magnetically conductive section is understood in the present case in particular as a section comprising a material which has a permeability value and/or a relative permeability $\mu_r$ which amounts to at least 10, in particular a section comprising a ferromagnetic material. By moving a permanent magnet outside of the magnetic influence with the magnetically conductive section of the coupling element the magnetic force applied by the magnetically conductive section upon a counter element is weakened, in particular at least essentially eliminated, so that the magnetic coupling is released. This way, preferably an adjustment path for the decoupling can be reduced by adjusting a permanent magnet into an unlocked position. In particular when in one embodiment a coupling element includes a yoke comprising a magnetically conductive material, around which an optionally electrified coil is arranged, in one embodiment generally a magnetic assembly may be formed integrally with the coupling element, in particular an electromagnet.

In order to couple an instrument module and instrument part of a surgical instrument, according to one aspect of the present invention at least one electromagnet of the magnetic assembly of the instrument module is activated and/or electrified, and this way preferably a currentless open coupling is closed between the coupling element and the counter element. For the purpose of decoupling, the electromagnet is accordingly deactivated and/or kept free from electricity.

Additionally or alternatively at least one permanent magnet of the magnetic assembly of the instrument module may be adjusted into the locked position. For the purpose of decoupling the permanent magnet is accordingly adjusted into the unlocked position.

In particular for the purpose of locking a currentless closed coupling between the coupling element and the counter element, in one embodiment for the coupling of an instrument module and an instrument part of a surgical instrument at least one electromagnet of the magnetic assembly of the instrument module, which additionally includes at least one permanent magnet, is deactivated and/or deenergized. For the decoupling, the electromagnet is accordingly activated and/or electrified.

In one embodiment, the coupling element and the counter element and/or the coupling element and the counter element assembly can be or are connected, in addition to the magnetic coupling, in a form-fitting fashion, preferably in order to center them in reference to each other and/or to fix them in a torque-proof fashion. In particular, either the coupling element or the counter element may include at least one eccentric projection, which engages a respective recess in the other one coupling element of counter element or a sterile barrier arranged between them, in particular a coupling part of such a barrier, when the coupling element and the counter element, perhaps via a barrier, are coupled to each other. The magnetic coupling can axially secure this form-fitting connection in one embodiment.

Similarly, one of the coupling element and the counter element may engage like a pin in a sheath section and/or socket section of the other one of the coupling element and the counter element when the coupling element and the counter element are coupled, with in particular the coupling element engaging a sheath section and/or socket section of the counter element or the counter element like a pin engaging a sheath section and/or a socket section of the coupling element. This way, in one embodiment the coupling element and the counter element can be fixed in a form-fitting fashion perpendicular in reference to their longitudinal extension, with the magnetic coupling fixing them in the direction of their longitudinal direction in a force-fitting fashion.

In one embodiment the instrument module and/or the instrument part can be sterilized and/or they are sterile. In particular when the instrument module and/or the instrument part comprise an electromotive drive for actuating an end effector of the instrument it may be difficult to sterilize it. Thus, in one embodiment, in particular a sterile barrier may be arranged and/or present between the coupling element assembly and the counter element assembly. The sterile barrier may in particular be embodied in a flexible fashion, at least in the coupling section, in order to allow following a motion of the coupling element and the counter element for actuating the end effector under an elastic deformation.

In one embodiment the sterile barrier comprises a coupling part for a magnetic coupling of a counter element to a coupling element. The coupling part may be connected in a mobile fashion via a seal to the remaining barrier, in particular a film, or be connected fixed thereto, in particular embodied in an integral fashion. This way a mechanical force transmission can be improved beyond the barrier. In one embodiment the coupling part comprises a magnetically conductive material in order to improve the magnetic coupling.

In particular when the coupling element and the counter element are centered towards each other, in particular in a form-fitting fashion, it may be advantageous for the coupling element and/or the counter element to be supported with play in a guide of the instrument module and/or the instrument part. This way the coupling element and/or the counter element may compensate a certain lateral offset during the coupling process.

In one embodiment the coupling element and the counter element are embodied like tappets and/or shafts and coupled to each other abutting and/or at their faces, with the magnetic assembly pulling the coupling element and/or the counter element in the direction of their preferably aligned longitudinal extension towards each other, in order to transmit tensile forces and/or torque.

In one embodiment of the present invention the coupling element and the counter element assembly may be advantageously coupled to each other in a sterile, compact fashion and/or at least essentially without play and slippage and/or without any visual control, and/or decoupled from each other.

In particular when a coupling element and a counter element are coupled to each other magnetically in a torque-proof fashion, this may result, in particular without any additional form-fitting connections or in case of ambivalent form-fitting connections, such as via a Hirth-gear, that the angular position of the counter element in reference to the instrument module is not unambiguously known after the coupling process. However, this is mandatory in minimally invasive robotic surgery, in which the intra-corporeal end effector is precisely actuated by the extracorporeal drive.

Thus, according to one aspect of the present invention, which preferably can also be combined with the above-stated aspects, an instrument module may include a coupling element assembly with one or more rotationally supported coupling elements which can be coupled detachably at rotationally supported counter elements of a counter element assembly of an instrument part, by which an end effector of a surgical instrument can be actuated, which comprises the instrument module and the instrument part coupled thereto.

In one embodiment the coupling element and the counter element (assembly) may be coupled and/or can be coupled to each other in a form-fitting fashion, in particular by way of gears, preferably Hirth-gears or spur-gears. If a sterile barrier is arranged between the coupling element and the counter element assembly, in one embodiment the coupling element and the counter element (assembly) may be coupled and/or can be coupled in a form-fitting fashion to a coupling part which preferably is supported rotationally in said barrier.

In general, the coupling element and the counter element (assembly) according to this aspect of the present invention can be coupled to each other in two or more different alignments, with in the present case in particular a rotary orientation and/or position between the coupling element and the counter element about its rotary axis is considered the orientation. These orientations may represent discrete orientations. In a simple case, one of a coupling element and a counter element shows one or more projections which may engage respective recesses in at least two orientations between the coupling element and the counter element in the other one of the coupling element and the counter element. Similarly, the coupling element and the counter element may include corresponding gears, which engage gears offset by the respective orientation, and this way can couple the coupling element and the counter element. The different orientations may also be geometrically undetermined and/or arbitrary, for example by an electromagnet being activated in a coupling element and a ferromagnetic section of the counter element, fixing it in this orientation with its plane face contacting the plane face of the coupling element in an arbitrary orientation.

In particular in order to allow in such couplings, which are possible in several orientations between the coupling element and the counter element, actuating the end-effector via the drive, preferably without prior calibration, the instrument module includes in one embodiment an angle sensor for detecting the angular position of the coupled counter element assembly, in particular a transmitter, in particular in one or more counter elements. The angle sensor may have several individual sensors each for detecting an angular position of a coupled counter element. The counter element or elements of the counter element assembly include respectively appropriate torque-proof transmitters, which are implemented to be detected by the angle sensor of the instrument module, in particular an individual sensor.

For a more compact illustration, in the present case the multitude of angular positions of two or more, in particular of all counter elements of the counter element assembly, is generally called an angular position of the counter element assembly in the sense of the present invention. An angular position of this counter element may in particular represent an orientation and/or rotary position of this counter element in reference to the instrument module, in particular in reference to a point fixed at the housing or the rotary bearing. Similarly, an angular position of a counter element may represent an orientation and/or rotary position of this counter element in reference to the coupling element coupled thereto.

In one embodiment the angle sensor is implemented to detect, in addition to an orientation and/or rotary position of the coupling element coupled to the counter element in reference to the instrument module, in particular in reference to a point fixed at the housing and/or the rotary bearing. In one further development, from this information, in particular by an addition of the correct algebraic sign, with the angular position of the counter element in reference to the coupling element coupled thereto, the angular position of the counter element can be determined in reference to a point fixed at the housing and/or the rotary bearing. Similarly, from the angular position of the counter element in reference to a point fixed at the housing or the rotary bearing, inversely the angular position of the counter element can be detected and/or determined in reference to the coupling element coupled thereto.

The angle sensor may be implemented for a touch-less detection of the angular position of the counter element assembly and/or the angular position(s) of the transmitter and/or the transmitters. In particular it may represent a magnetic, electric, capacitive, and/or optic angle sensor. The transmitter or transmitters, with its/their north-south axis preferably at least essentially being oriented perpendicular in reference to the rotary axis of the counter element, may include a transponder, preferably a RFID-system, an optic marking, or the like.

In one embodiment, the angle sensor is embodied as an absolute value transmitter and/or embodied to detect an absolute angular position of the counter element assembly in reference to the instrument module and/or the coupling element, for example via an absolute-coded transmitter or receiver. The coding may have an angular range of 360° (so-called single-turn absolute value transmitter) so that the angle sensor reads two angular positions, distorted by 360°, as the same angular position. In another embodiment the coding may have an angular range of more than 360° (so-called multi-turn absolute value transmitter) so that the angle sensor detects two angular positions distorted by 360° as different angular positions. Preferably the angular position is available in an absolute value transmitter directly after the coupling and detecting of the angle sensor without any distortion of the counter element assembly being required.

In another embodiment the angle sensor is embodied as an incremental value transmitter and/or for the purpose of only detecting an angular change of the counter element assembly in reference to the instrument module and/or the coupling element. In a further development the transmitter or receiver is distance-coded or has one or more reference marks. Upon crossing a reference mark, the angular position can then be detected by integrating and/or adding the incremental values and/or angular changes.

In one embodiment a surgical instrument comprises several instrument parts, which can optionally be coupled to the instrument module, with the counter element assemblies of the different instrument parts have differently coded transmitters, which are implemented to be detected by the angle sensor of the instrument module, with the angle sensor additionally being implemented to detect the coding of the transmitter and this way identify the coupled instrument part. This way, the functionalities can determine on the one hand the orientation of the counter element assembly and on the other hand identify the instrument part coupled thereto, by which the transmitter or transmitters and the angle sensors is/are implemented. In one embodiment a permanent magnet can also serve or be used as a transmitter for detecting the angular position and for the magnetic coupling.

During or after the coupling of the instrument part to the instrument module in one of multiple orientations, according to one aspect of the present invention, the angular position of the coupled counter element assembly of the instrument part is detected, in particular in reference to the coupling element assembly or a point fixed at the housing of the instrument module, using the angle sensor of the instrument module. This way, after the detection, the orientation of the counter element or elements, and thus preferably also a position and/or coordinate of the end effector are known, so that in one embodiment the end effector can be correctly actuated by a drive without recalibration.

In one embodiment, a context, in particular a calibration offset between the angular position of the counter element assembly and an end effector position, is detected in advance and saved. After coupling the counter element assembly the end-effector position can be determined from the angular position of the counter element assembly, detected by the angle sensor, in consideration of said context.

BRIEF DESCRIPTION OF THE DRAWINGS

Additional advantages and features are discernible from the dependent claims and the exemplary embodiments. For this purpose it is shown, partially schematically:

FIG. 22 a part of a surgical instrument according to one embodiment of the present invention in a longitudinal cross-section;

FIG. 23 a part of a surgical instrument according to another embodiment of the present invention in an illustration according to FIG. 1

FIG. 24 a part of a surgical instrument according to another embodiment of the present invention shown in FIG. 1, 2 in a respective illustration;

DETAILED DESCRIPTION

Figure 1:
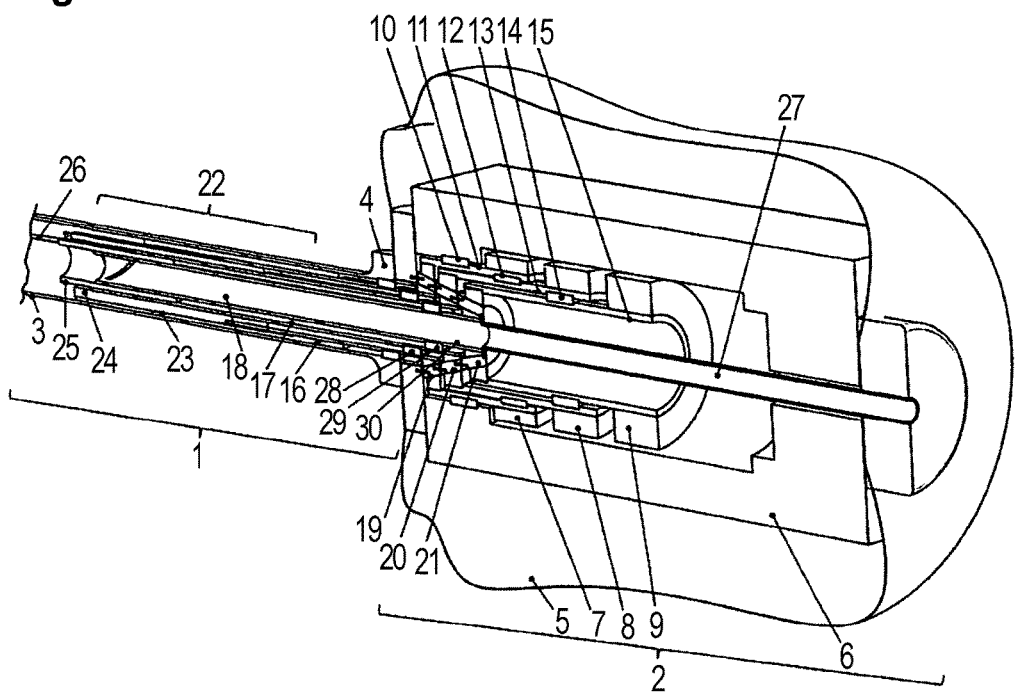
FIG. 1 a part of an instrument assembly of a robotic surgery system according to an embodiment of the invention in a perspective cross-section, FIG. 2 a transmission at the side of the instrument according to another embodiment of the present invention.

FIG. 1 shows a part of an instrument assembly of a robotic surgery system according to one embodiment of the invention in a perspective cross-section.

The instrument assembly comprises an instrument 1, a drive unit 2 connected thereto, and an instrument interface with a sterile cover 5 arranged between the drive unit and the instrument.

In this exemplary embodiment the rotary axes of the drive unit coincide with a shaft axis of the instrument. This concept is in particular suitable for instruments actuated with tensile/thrust rods.

The sterile surgical instrument 1 is shown in FIG. 1 at the left side, the drive unit 2 in FIG. 1 at the right side. The instrument 1 is mechanically attached in a detachable fashion to a housing 6 of the drive unit 2 via a connection flange 4 at a proximal end of the instrument shaft 3. The drive unit 2 is encompassed by a sterile cover 5 in order to prevent any contamination of the surgery area.

In this exemplary embodiment, three independent rotary drives are respectively located in the housing 6 of the drive unit 2, each comprising a drive shaft 10, 13, and/or 15 and a corresponding electromotor 7, 8, and/or 9. The drive shafts 10, 13, 15 are embodied as hollow shafts and arranged coaxially in reference to each other. The drive shaft 10 is supported entirely at a bearing site 11 in the housing 6. The inner drive shaft 13 is supported with a bearing 12 in the drive shaft 10, the drive shaft 15 with a bearing 14 in the drive shaft 13. This concept advantageously allows, primarily in the radial direction, a very compact design of the detachable instrument interface. Thus, in a multi-robot application the risk of collisions between individual robots can be considerably reduced due to the shorter allowable minimum distance between the instruments.

The symbolic illustrations of the electric motors 7, 8, 9 include additional components required for a regular operation, such as transmissions and/or sensors, for example. Preferred embodiments are concentrically arranged motor units, which can be implemented either as direct drives or as motors with reduction gears arranged downstream, for example planetary gears or harmonic-drive gears.

In a modification, not shown, the rotary drives may be radially offset electric motors, which respectively drive the drive shafts with a spur gear or friction wheel drive, or have orthogonally offset electric motors, which drive the drive shafts respectively with a worm drive, helical drive, or crown wheel gears.

Figure 10A:
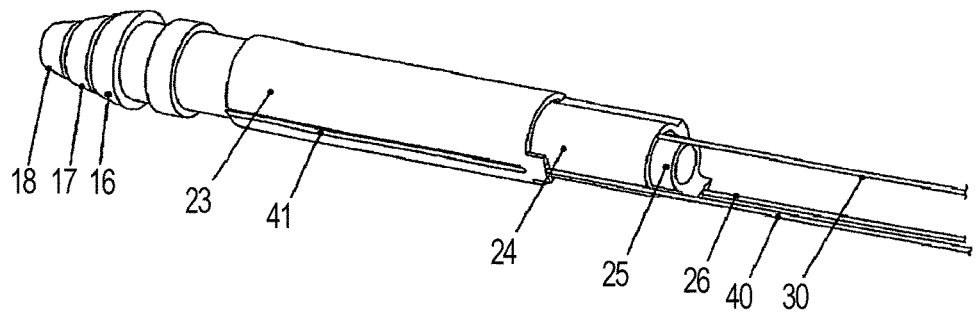
FIGS. 10A, 10B a transmission according to one embodiment of the present invention in two perspective views.
Figure 10B:
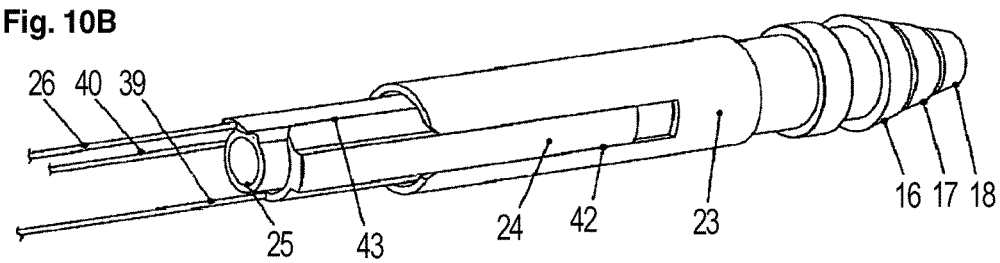

The nested drive shafts 10, 13, and 15 are continued at the instrument side in the form of drive shafts 16, 17, and/or 18, which are also embodied as hollow shafts and which are arranged coaxially in reference to each other. The support of the drive shafts 16, 17, and 18 at the instrument side is embodied as fixed/floating bearings 28, 29, 30, arranged at the proximal end of the instrument shaft 3. The shaft 16 is radially and axially supported at the bearing site 28 in the instrument shaft 3. The interior drive shaft 17 is supported with the bearing 29 in the drive shaft 16, the drive shaft 18 with the bearing 30 in the shaft 17. The sliding sheaths 23, 24, and 25 act as loose bearings, which simultaneously are components of a transmission 22 at the instrument side for the conversion of the rotational drive motion into a translational motion of the tensile and/or thrust means 26, 39 and/or 40 (cf. FIGS. 10A, 10B). They finally transmit the drive motion to the instruments and/or end effector degrees of freedom at the distal end of the instrument shaft 3.

FIG. 1 shows as an example only one tensile and/or thrust means 26, although for each degree of freedom of the instrument a separate transmission link being provided. Examples for such tensile and/or thrust means are pulleys, Bowden-pulleys, or tensile/thrust rods.

In order to connect the drive shafts 10, 13, and 15 of the drive unit to the drive shafts 16, 17, and 18 at the instrument side a coupling mechanism is provided, which simultaneously represents a sterile barrier between the instrument and the non-sterile drive unit. The coupling shown as an example in FIG. 1 is a conical coupling, which transmits the drive moments via friction-fitting or form-fitting means.

By this design principle the drive shafts 15 and 18, located inside in the coaxial arrangement, can be embodied as hollow shafts as well. This way sufficient space remains in the center of the instrument shaft 3 in order to guide additional drive means, for example a Bowden pulley, a rotary shaft with an elastic section in the area of the multiple link to drive an end effector, and/or an auxiliary instrument, in particular an electric line, a hose, or the like. Another potential application of this design principle is the insertion of special surgical instruments through the center of the instrument shaft.

In order to ensure the sterility of the elements guided through the center of the instrument even in the area of the drive unit 2, the sterile barrier with an inner passage in the form of a sterile guiding tube 27 also extends through the entire drive unit 2, as described in the following.

Figure 2:
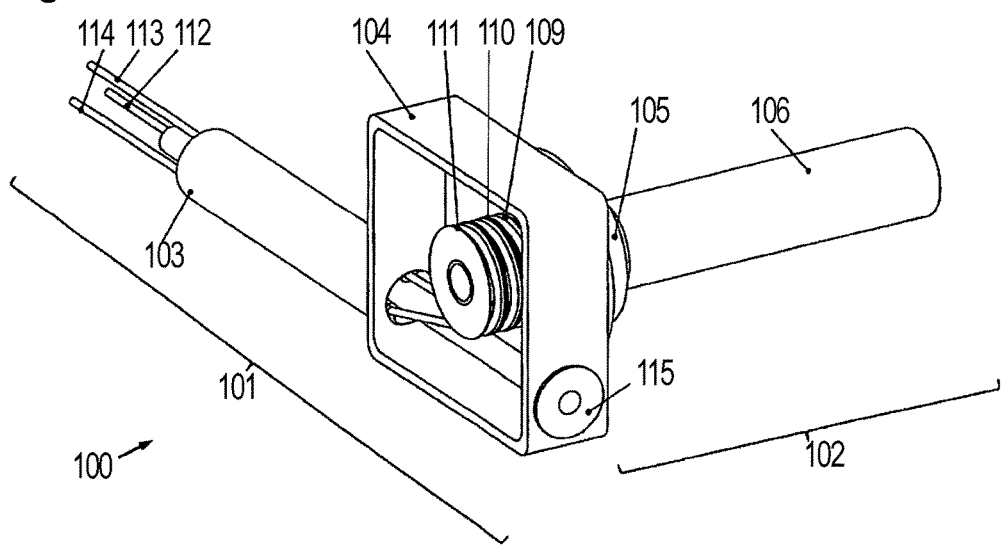

FIG. 2 shows a transmission 100 at the instrument side according to another embodiment of the present invention, in which the axes of the drive shaft and the shaft are orthogonal. This arrangement is in particular suitable for instruments which are actuated with pulleys. However, it can also be used for instruments with tensile/thrust rods, in which the transmission at the instrument side can be realized for the transmission of the rotation of a drive shaft into a translation of a tension and/or thrust means, for example as a push-crank mechanism.

A housing 104 is located at the proximal end of the instrument 101, connected fixed to the instrument shaft 103. The instrument 101 is connected at the proximal end via a sterile barrier 105 to the drive unit 102 (with its housing not being shown). The drive shafts 106, 107, and 108 are coaxially arranged in the drive unit 102 in order to achieve dimensions as compact as possible. They are continued at the instrument side respectively as a pulley 109, 110, and/or 111. The connection of the shaft sections respectively occurs via the sterile intermediate coupling sections 116, 117, and 118, which are rotational in reference to each other.

An intermediate coupling element 118 of the exterior drive shaft 106 is connected to the sterile barrier 105 and rotationally supported therein. In the exemplary embodiment the drive shafts of the drive unit and the instrument are coupled in a form-fitting fashion to a sprocket coupling, which is described in greater detail with reference to FIG. 6.

The pulleys 112, 113, and 114 actuating the degrees of freedom of the instrument are wound about the pulleys and/or drive shafts 109, 110, and/or 111 at the instrument side, so that the force flux is closed between the drive shafts 106, 107, and 108 and the degrees of freedom of the instrument. Optionally, a tubular passage 115 may be provided, which for example can be used for guiding an auxiliary instrument, in particular a media line, to the distal end of the instrument shaft 103.

Detachable Coupling with Sterile Barriers for at Least One Rotary Drive Train

In order to connect the instrument to the drive unit, a simple, detachable coupling mechanism is provided, which simultaneously represents the sterile barrier between the instrument and the unsterile drive unit.

Figure 4:
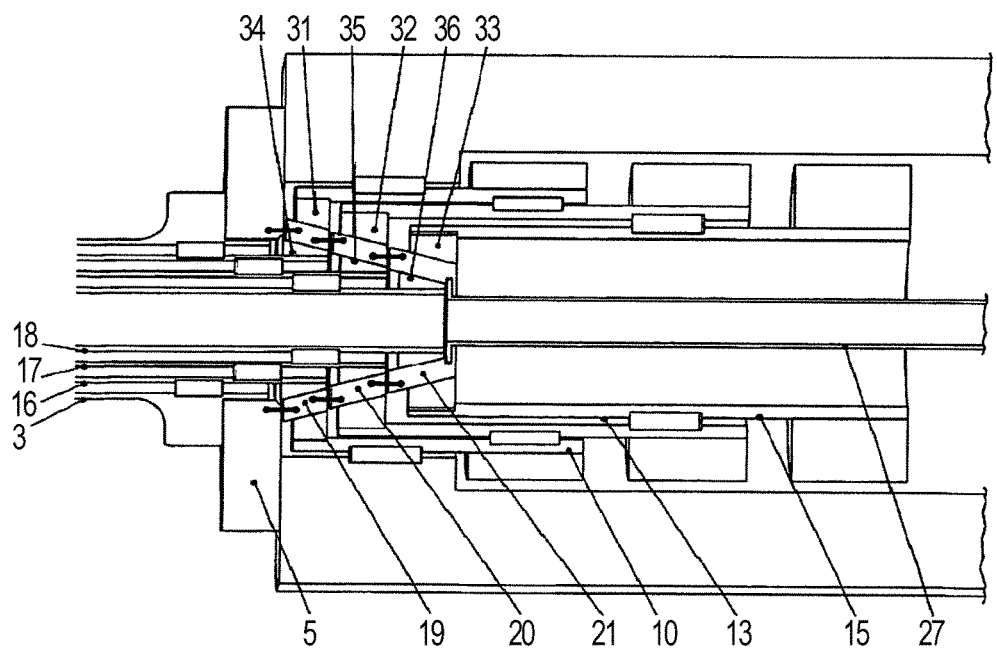
FIG. 4 a cross-section of a conical coupling of an instrument assembly according to one embodiment of the present invention.

FIG. 4 shows in a cross-section the conical coupling of the exemplary embodiment of FIG. 1 with a sterile barrier. The coupling assembly transmits the drive moments from the drive shafts 10, 13, and 15 by way of friction-fitting or form-fitting means to the drive shafts 16, 17, and 18 at the instrument side. At the proximal ends of the hollow shafts 16, 17, and 18 at the instrument side, coupling parts are arranged in the form of exterior cones 34, 35, and 36, which are connected fixed to the respective hollow shaft. At the distal ends of the drive shafts 10, 13, and 15 the coupling parts 31, 32, 33 are arranged with inner cones. The connection of the ends of the shaft occurs via conical intermediate elements 19, 20, and/or 21, which act as sterile barriers. These elements are connected to each other and also to the sterile barrier 5 in a sealed fashion. These connections only serve for the simple handling during the installation of the sterile barrier; however, they allow otherwise all motions required for moving the intermediate elements, in particular a rotation of the drive shafts. Simultaneously these intermediate elements 19, 20, and/or 21 represent a gap seal and/or labyrinth seal between the coupling parts.

The coupling parts 31, 32, 33 arranged at the drive shafts 10, 13, and 15 are each connected to a shaft in a torque-proof, however axially displaceable fashion, for example by a geared or a polygonal shaft profile. This way, the axial pre-tension required for transmitting force can be applied by springs, for example, acting upon the coupling parts at the driving side. Simultaneously, a potential axial offset is compensated of the shaft sections between the drive side and the instrument side.

Figure 5A:
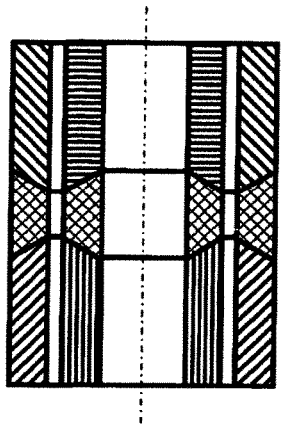
FIGS. 5A-5D additional embodiments of such a conical coupling.
Figure 5B:
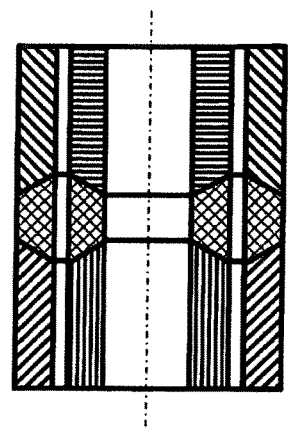
Figure 5C:
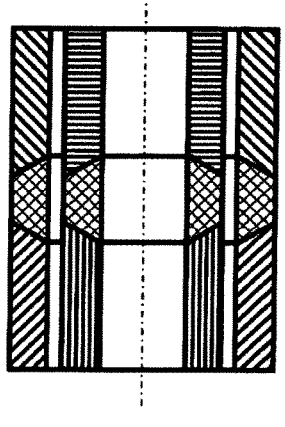
Figure 5D:
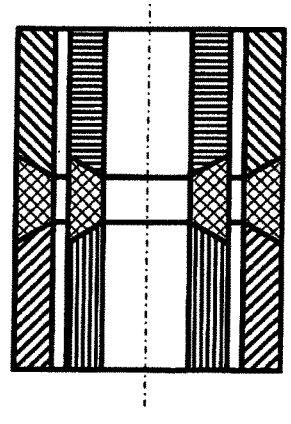

Instead of the combination of the inner cones at the driving side and the outer cones at the instrument side, for each pairing an inner and an outer drive shaft of the drive unit and the instrument is possible and additional arrangements as well, which are sketched in FIGS. 5A-5D according to the following configurations:

| Coupling part 31/32/33, 34/35/36 | FIG. 5A | FIG. 5B | FIG. 5C | FIG. 5D |
|---|---|---|---|---|
| Inner hollow drive shaft of the drive unit | Inner cone | Outer cone | Inner cone | Outer cone |
| Inner hollow drive shaft of the instrument | Inner cone | Outer cone | Inner cone | Outer cone |
| Outer hollow drive shaft of the drive unit | Outer cone | Inner cone | Inner cone | Outer cone |
| Outer hollow drive shaft of the instrument | Outer cone | Inner cone | Inner cone | Outer cone |

Figure 3:
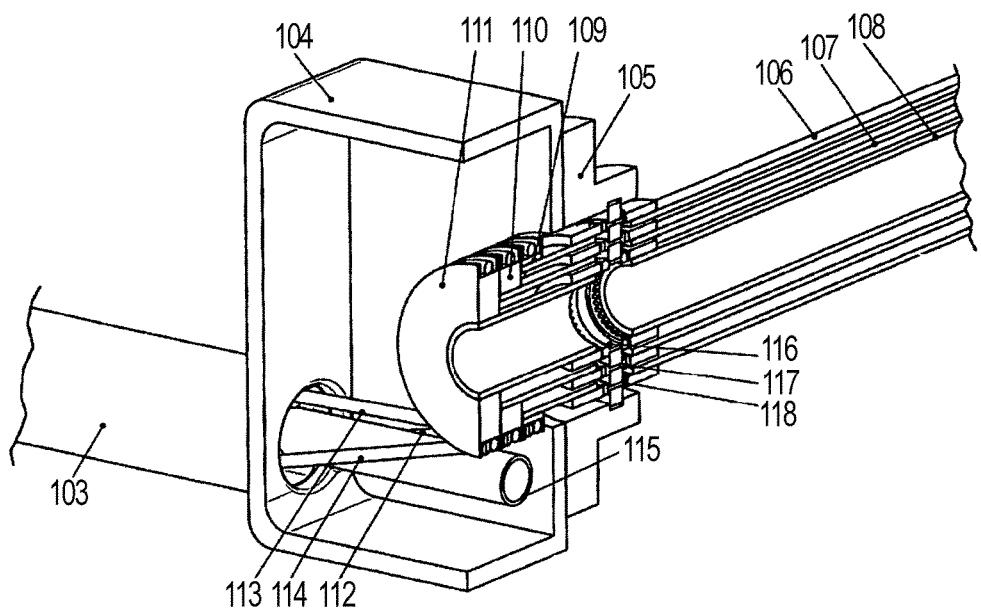
FIG. 3 a transmission of FIG. 2 in another perspective cross-section.
Figure 6:
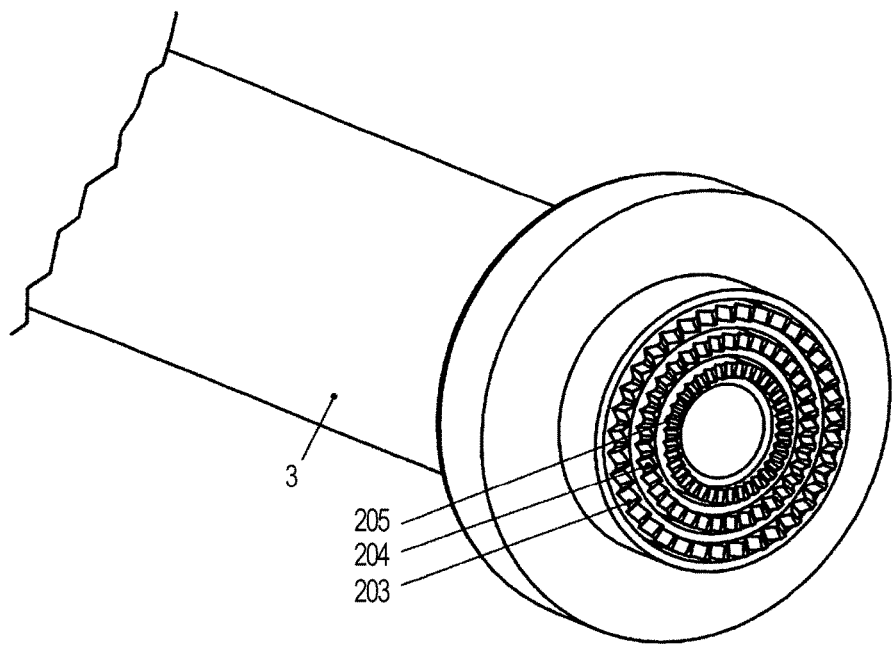
FIG. 6 another shaft coupling of an instrument assembly according to an embodiment of the present invention.
Figure 7:
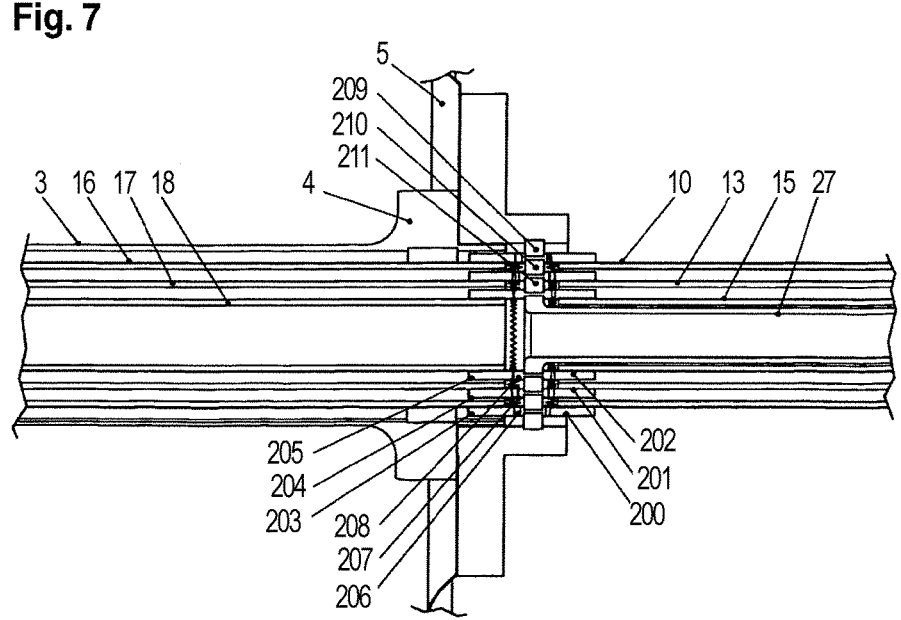
FIG. 7 a cross-section of this shaft coupling of FIG. 6.

FIG. 6 shows a shaft coupling with a sterile barrier, which transmits the drive moments in a form-fitting fashion via the spur gears, for example a Hirth-gear, from the drive shafts 10, 13, and 15 to the drive shafts 16, 18 at the instrument side, FIG. 7 shows a cross-section of this shaft coupling. Instead of the conical coupling of FIG. 4, 5, in particular the shaft coupling can be provided in an instrument assembly according to FIG. 1, 2 or 3.

For this purpose, at the proximal coupling parts of the hollow shafts 16, 17, and 18 at the instrument side spur gears 203, 204, 205 are applied, which are connected fixed to the respective hollow shaft. At the distal ends of the drive shafts 10, 13, 15, the coupling parts are arranged in the form of sliding sheaths with spur gears 200, 201, 202. The connection of the shaft ends occurs via sheath-like intermediate elements 206, 207, and 208 with spur gears at both sides, which act as sterile barriers. The intermediate sheaths 206, 207, 208 are connected to each other and to the sterile barrier 5 by the fastening rings 209, 210, 211. The inner passage and/or the sterile guide tube 27 are connected this way to the innermost intermediate sheath 208 so that the entire arrangement represents a sterile barrier with gap seals. The intermediate sheaths 206, 207, 208 only serve for the simple handling during the installation of the sterile barrier, however otherwise they allow all motions required for the function. They act as gap and/or labyrinth seals.

The sliding sheaths 200, 201, 202 arranged on the drive shafts 10, 13, and 15 are each connected to the shafts in a torque-proof yet axially displaceable fashion, for example by a geared or polygonal shaft profile. This way the axial pre-stressing necessary for transmitting force can be applied for example by springs which act upon the sliding sheaths 200, 201, 202. Simultaneously a potential axial offset is compensated between the shaft sections at the drive side and the instrument side.

Figure 8:
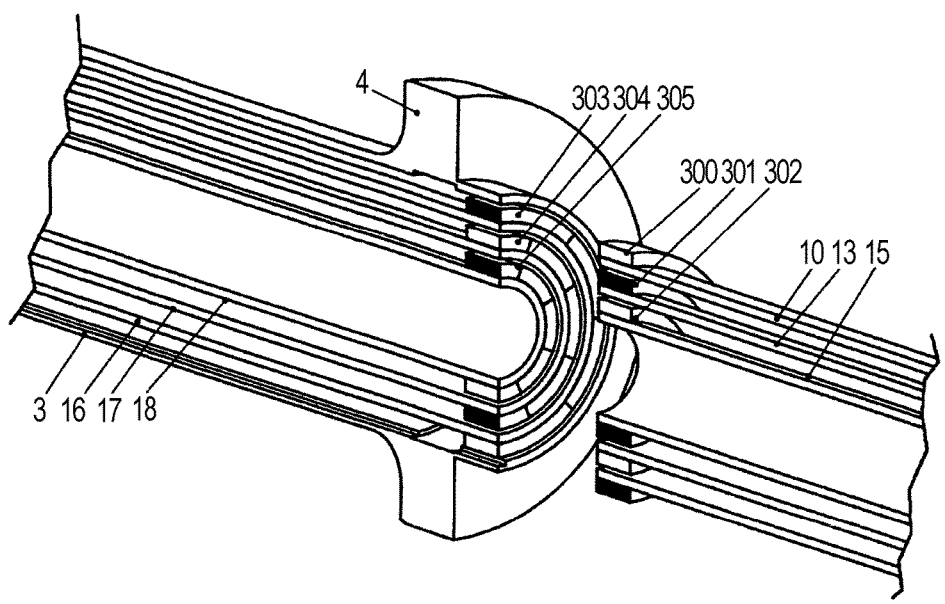
FIG. 8 a magnetic coupling of an instrument assembly according to one embodiment of the present invention.

Another variant of the shaft coupling with sterile barriers is the magnetic coupling shown in FIG. 8. The shaft coupling may be provided instead of the conical and/or shaft coupling of FIGS. 4 to 7, in particular in an instrument assembly according to FIG. 1, 2 or 3.

Coupling parts in the form of magnetic rings 200, 201, and/or 202 are fixed at the distal ends of the drive shafts 10, 13, and 15. Similar thereto, coupling parts are fixed in the form of magnetic rings 203, 204, and/or 205 at the hollow shafts 16, 17, and 18 respectively at the instrument side. All magnetic rings 200 to 205 are sectionally magnetized and aligned towards each other with a preferably small axial distance and/or air gap in order to allow transmitting the highest possible drive moments. The strength of the moment that can be transmitted depends, in addition to the air gap, also on the magnetic field strength and the number of magnetic sectors.

Figure 9:
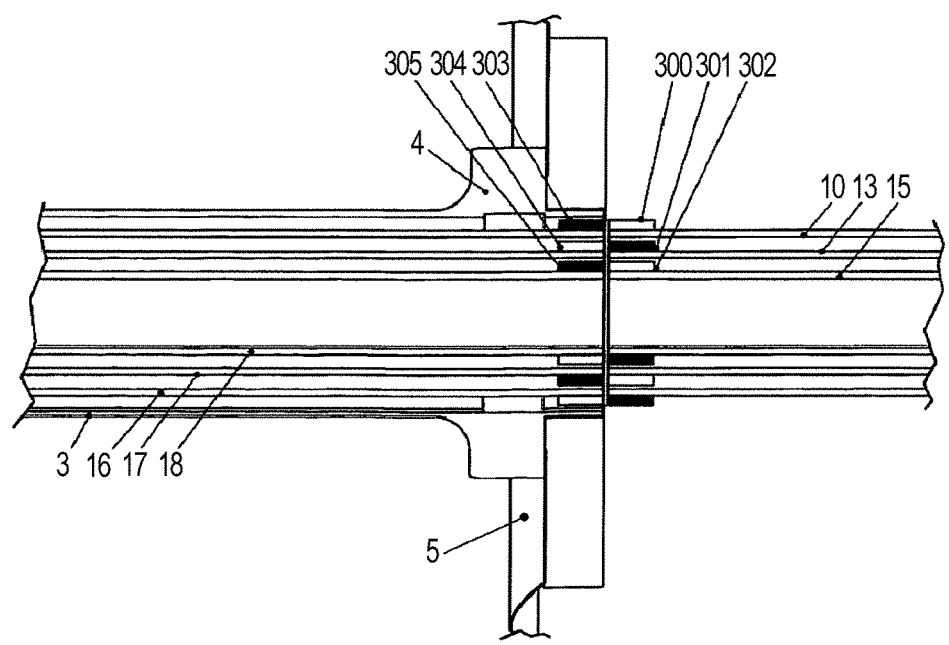
FIG. 9 the magnetic coupling of FIG. 8 in a cross-section.

FIG. 9 shows in a cross-section a magnetic coupling with sterile barriers. The magnetic rings are aligned towards each other with minimal axial distance in order to allow transmitting the highest possible drive moments. An advantageous feature of this coupling principle is the simple design of the sterile cover 5. Due to the narrow axial air gap of the magnetic coupling a simple film can be used and no specially formed part is necessary.

Implementing the Rotation-Translation Movement Type at the Instrument Side

In one embodiment of the present invention only rotary drives are used. The drive trains in robotic guided surgical instruments however use, due to the tight design space inside the instrument shaft, primarily pulleys or tension/thrust rods for transmitting the drive motions to the distal end of the instrument. Thus, according to the above-described detachable instrument interface, a transmission 22 is provided at the instrument side in order to convert the rotary drive motion into a translational motion of the pulleys or tension/thrust rods.

FIG. 10 shows in two perspective illustrations a converting transmission 22 according to one embodiment of the present invention, in which a separate sliding sheath is provided for each drive shaft. In the case shown here, the three sliding sheaths 23, 24, and 25 convert the rotation of the drive shafts 16, 17, and 18 into a translation of the tension and/or thrust means 26, 39, and 40. The sliding sheaths 23, 24 and 25 act simultaneously as a distal loose bearing for the hollow shafts 16, 17, and/or 18. The sliding sheaths themselves only have a translational degree of freedom, which allows the displacement along the axis of the shaft. The restriction of the degree of freedom of the sliding sheaths 23, 24 and 25 is achieved by groove-guides 41, 42, and 43, which are nested in each other. The sliding sheaths 23, 24, and 25 are inserted into each other such that a sheath positioned outside accepts the bearing of the sheath located inside. This way, a very compact design is achieved.

Accordingly, the exterior sliding sheath 23 is supported in the instrument shaft 3. A transitional fitting between the sheath 23 and the shaft 3 serves as a radial bearing. A rotation of the sheath 23 is blocked by a feather key 41 fixed at the sheath 23, gliding in a groove inserted in the instrument shaft 3. The sliding sheath 24 is supported in the exterior sliding sheath 23. A transitional fitting between the sheath 24 and the sheath 25 serves as a radial bearing. A rotation of the sheath 24 is blocked by the groove guide 42. The inner sliding sheath 25 is supported in the sliding sheath 24. A transitional fitting between the sheath 25 and the sheath 24 serves as a radial bearing. A rotation of the sheath 25 is blocked by the groove guide 43.

Figure 11:
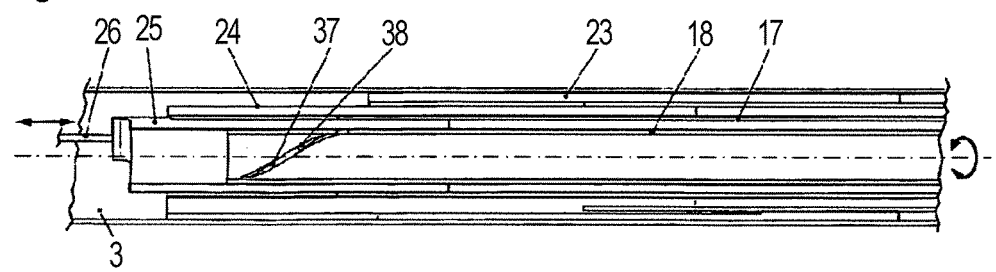
FIG. 11 an enlarged cross-section of the transmission of FIGS. 10A, 10B.

The coupling of the drive shafts to the sliding sheaths is done with a guiding groove, with its functionality being explained as an example with reference to the hollow shaft 18 located at the inside, and FIG. 11, which shows an enlarged cross-section. A helical groove 37 is inserted at the distal end of the hollow shaft 18. A pin 38, which is fixed at the sliding sheath 25, engages the helical groove 37 in a form-fitting fashion. Thus, a rotation of the hollow shaft 18 leads to a displacement of the sheath 25 along the axis of the shaft and thus also to an adjustment motion of the tensile and/or the thrust means 26. At the distal end of the sliding sheaths 23, 24, and 25 the tensile and/or thrust means 26, 39, and 40 are connected, which transfer the drive motion to the degrees of freedom of the instrument and/or an end-effector at the distal end of the instrument shaft 3.

One advantage of this solution is that the drive motions, in particular the adjustment angle and the angular speed, can be adjusted within every instrument to the respective requirements, as the incline of the guide bar determines the transmission ratio and the operating range. Thus, the drive unit can be used for the highest possible number of different instruments and the efficiency and user friendliness can be increased.

Figures 12A, 12B:
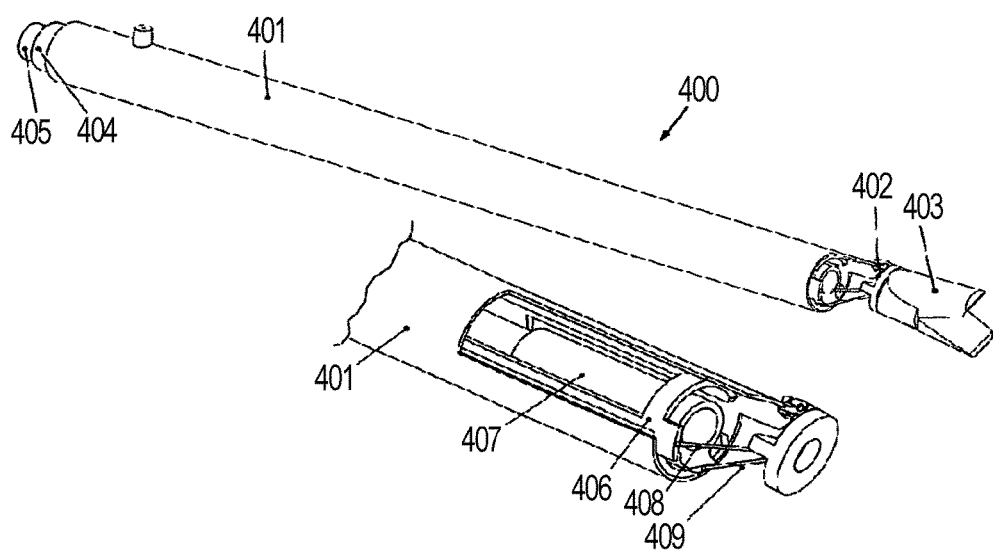
FIGS. 12A, 12B an instrument according to one embodiment of the present invention with a distal transmission in a perspective overall view (FIG. 12A) and/or an enlarged detail (FIG. 12B)

Instead of the proximal arrangement shown in FIGS. 10, 11, the transmission can alternatively also be arranged at the distal end of the instrument, thus as close as possible at the instrument kinematics and the end effector. FIGS. 12A and 12B show an instrument 400 according to an embodiment of the present invention with a distal transmission in a perspective, comprehensive view (top in FIG. 12A) and/or an enlarged detail (bottom in FIG. 12B).

The transmission is located at the distal end of the instrument 400 and thus near the instrument kinematics 402 and the end effector 403. The actuation of the distal joint 402, which in the example shown is embodied as a parallel kinematics, occurs with tensile and/or thrust means in the form of coupling rods 408 and 409, which are rotationally connected to the segment carrying the end effector. The respectively other ends of the coupling rods 408 and 409 are rotationally connected to the sliding sheath 406 and 407, which are displaced along the axis of the shaft for adjusting the angle of the joint. The sliding sheaths 406 and 407 are connected to the hollow shafts 404 and/or 405, with the conversion of the rotary drive motion into the translational feed motion of the sheath occurring via the guide bar mechanics described in reference to FIGS. 10A, 10B, and 11. Sufficient space remains in the center of the inner hollow shaft 405 in order to pass drive means through it, for example a Bowden pulley or a rotary shaft with a flexible section in the area of the multiple joint for driving the end effector 403 and/or an auxiliary instrument, in particular electric supply lines, hoses, or the like.

Contrary to the pulleys used in common instruments of minimally invasive robotic surgery, in this embodiment the drive performance is transmitted from the drive unit to the tip of the instrument via hollow shafts, coaxial in reference to the shaft of the instrument. This can yield a considerably higher resilience and stiffness of the drive train in reference to pulleys or thin solid shafts, so that advantageously higher driving forces can be transmitted. Accordingly this embodiment is especially recommended for instruments in which higher processing forces develop, e.g., devices for placing staple sutures.

Sterile Barrier Between the Drive Unit and the Instrument

Some components of the drive unit cannot tolerate the environmental conditions during a sterilization process. Accordingly, the instrument interface comprises a sterile cover which shields the drive unit during operation. In addition to the cover, which securely encompasses the housing of the drive unit and commonly is embodied as a film hose, the instrument interface between the drive unit and the instrument should allow the transmission of mechanic power and electric signals and simultaneously prevent any contamination of the surgery area by an unsterile drive unit.

Figure 13:
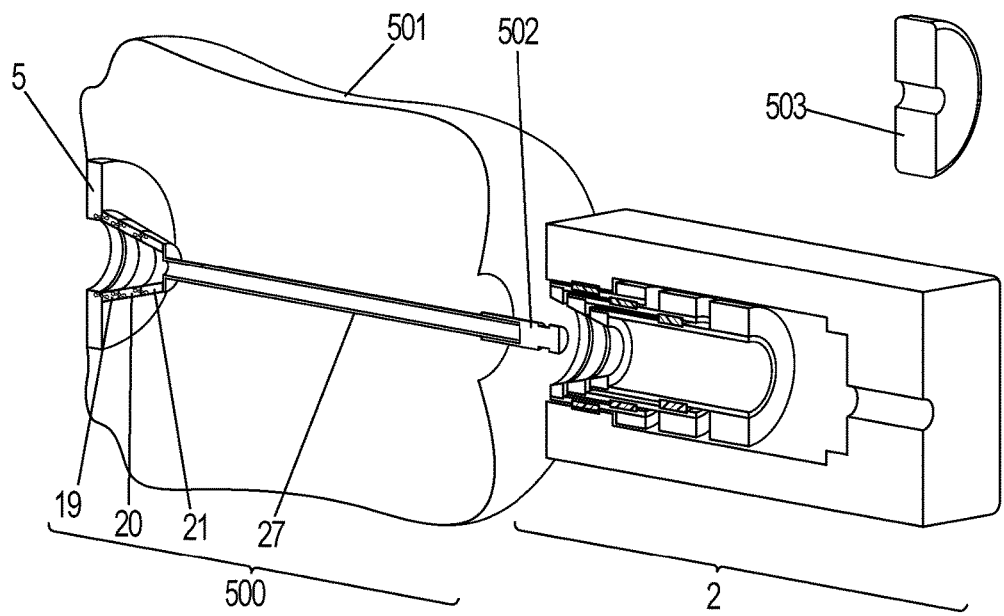
FIG. 13 an instrument interface according to one embodiment of the present invention.
Figure 14:
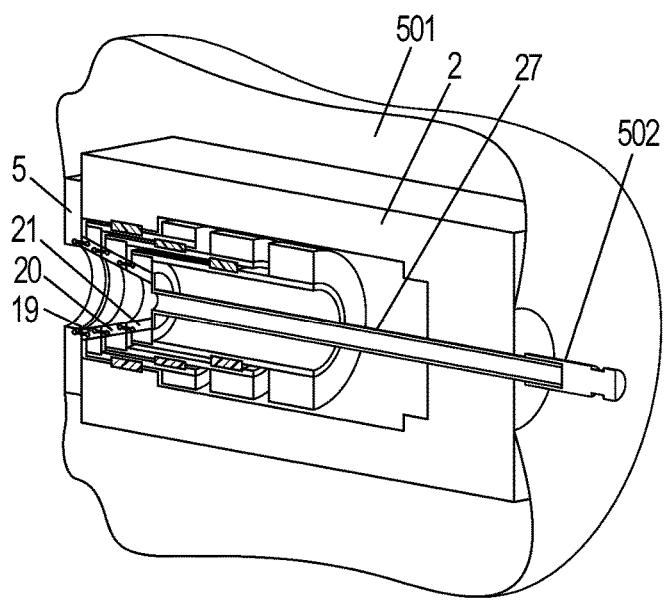
FIG. 14 the instrument interface of FIG. 13 with a connected blind plug.
Figure 15:
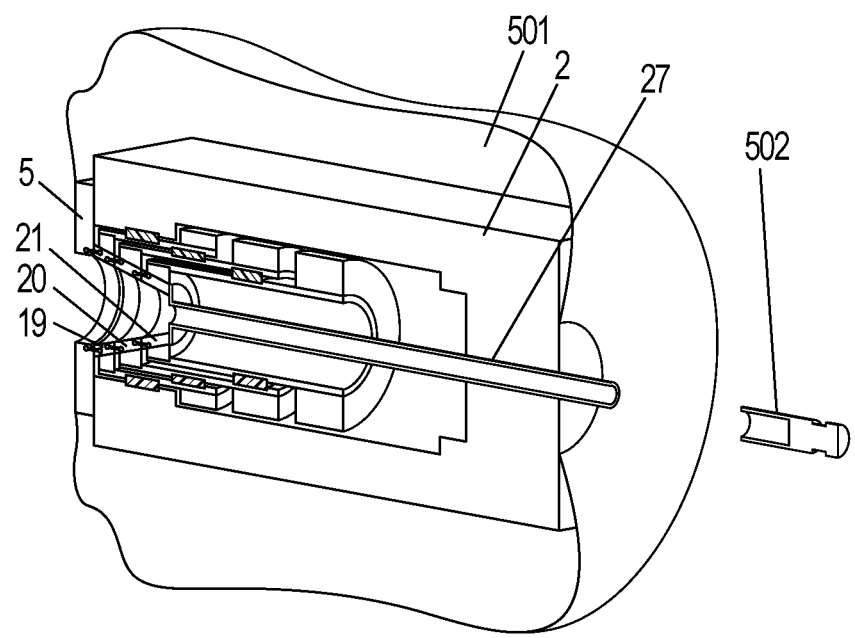
FIG. 15 the instrument interface of FIG. 14 with the blind plug removed.
Figure 16:
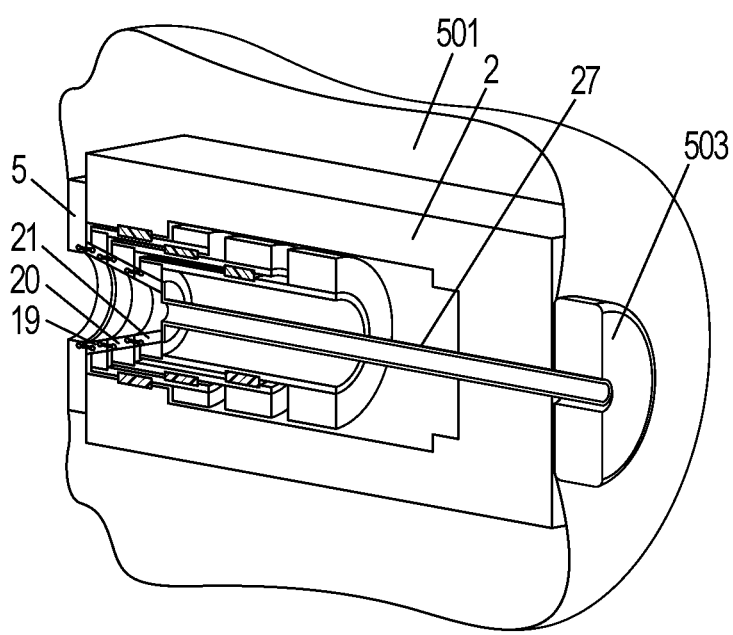
FIG. 16 the instrument interface of FIG. 15 with the cap ring connected.

FIG. 13 shows an overview of the instrument interface 500 with various partial components, which may be provided for example for the instrument assembly of FIG. 1.

The instrument interface 500 comprises a sterile film cover 501, which encompasses the housing of the drive unit 2, an inherently stable flange and/or instrument carrier 5, which for the purpose of coupling the drive trains, comprises for example the conical intermediate elements 19, 20, 21 described in reference to FIG. 4, as well as an inner passage in the form of the guiding tube 27. A connection ring 503 connects the guide tube 27 to the film cover 501. In order to ensure the sterility of the guide tube 27 during the insertion process into the drive unit 2 the guiding tube 27 is initially closed at its proximal end with a blind plug 502, which also covers a section of the jacket. The instrument interface 500 is designed as a comprehensive assembly, in which all parts are combined to form a unit. This way the handling is greatly simplified. In case of the magnetic coupling explained in reference to FIG. 8, a film is sufficient as a sterile barrier and/or instrument interface between the shaft sections.

Figure 17:
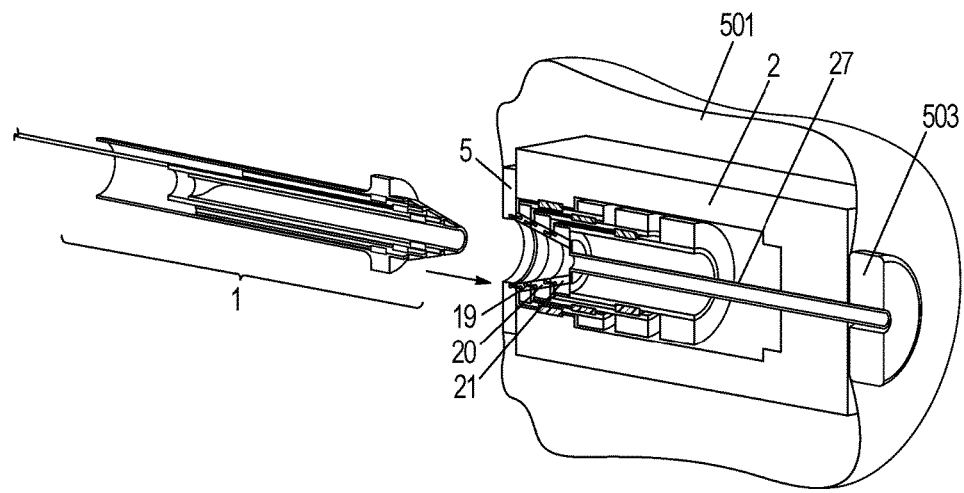
FIG. 17 the instrument interface of FIG. 16 with the instrument coupled.

The other FIGS. 14 to 17 illustrate the sterile packaging of the drive unit and the connection of a surgical instrument thereto. The instrument carrier 5 is placed onto the drive unit as the first step (cf. FIG. 14). Simultaneously the sterile guide tube 27 is inserted into the hollow shaft as well as the intermediate parts 19, 20, 21 of the shaft couplings into the drive unit 2, and the film cover is slid over the drive unit 2. Then the blind plug 502, which after passing through the sterile guide tube 27 has become unsterile due to the hollow shaft of the drive unit 2, is pulled off the guiding tube 27 and discarded by an unsterile member of the surgery team (cf. FIG. 15). Due to the fact that the blind plug 502 also covers a portion of the jacket of the guiding tube 27, the section of the guiding tube 27 projecting out of the drive unit 2 remains sterile. Finally, the sterile cover is sealed by a placement of the cap ring 503 onto the guiding tube 27 (cf. FIG. 16). FIG. 17 finally shows the docking of a surgical instrument 1 to the sterilely packaged drive unit 2.

Guiding Additional Drive Trains and/or Auxiliary Instruments Through the Instrument Shaft Towards the Distal End of the Instrument In addition to a simple mechanic design of the detachable instrument interface, the coaxial arrangement of all drive shafts offers the advantage that the center of the drive unit and the instrument are clear for additional driving means, for example pulleys, Bowden pulleys, and/or rotary shafts being guided through it to actuate the end effector. For example, a Bowden pulley can be used in duplicate; the cover serves for transmitting a first actuating force, the core of the transmission. Additionally, electric lines for monopolar or bipolar instruments, suction and rinsing hoses may be guided in the center of the instrument shaft. Similarly, other auxiliary instruments may also be guided by the robot, for example fiber optics for laser applications or flexible instruments for the argon-plasma coagulation, for cryosurgery, or water jet surgery, frequently used for tumor resection.

Figure 18:
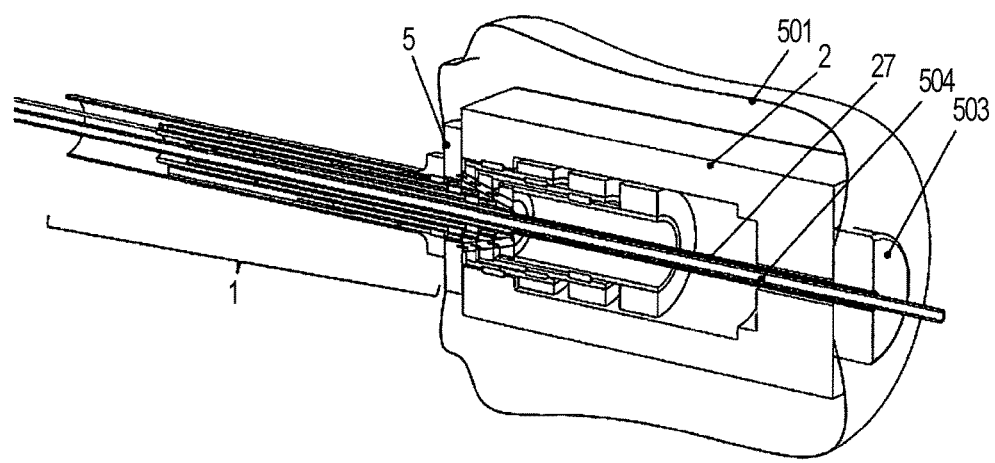
FIG. 18 an instrument assembly with an inserted auxiliary instrument according to an embodiment of the present invention.

FIG. 18 shows an instrument assembly with a stiff or flexible auxiliary instrument being inserted and/or guided through.

For this purpose, after the placement of the sterile cover 501, the auxiliary instrument 504 is advanced from the rear through the guiding tube 27 through the drive unit 2 to the distal end of the instrument 1 and fixed in this position. Subsequently, the auxiliary instrument 504 can be used like a common robot-guided instrument and be moved by the degree of freedom provided by the instrument 1 in the surgery area. In addition to the suitability for stiff and flexible auxiliary instruments this solution offers the advantage that no additional design space is required in the area of the detachable instrument interface in order to insert the auxiliary instrument 504 into the instrument shaft.

Figure 19:
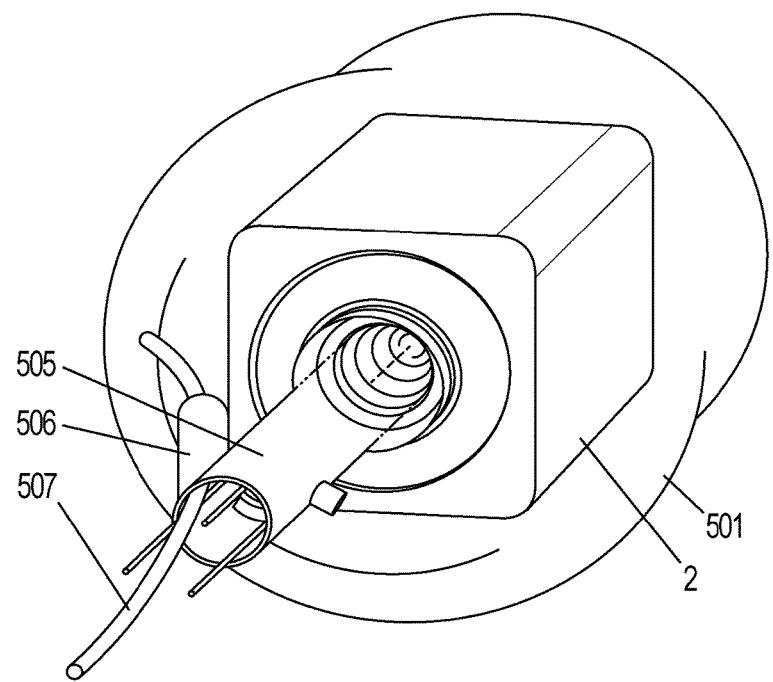
FIG. 19 a part of an instrument of an instrument assembly according to another embodiment of the present invention.

FIG. 19 shows a part of an instrument of an instrument assembly according to another embodiment of the present invention which is in particular suitable for flexible auxiliary instruments. Here, the auxiliary instrument 507 is not introduced through the drive unit 2, but through a curved tubular section 506, which is arranged at the instrument shaft 505 directly in front of the drive unit 2 and/or the instrument interface. In this solution a sterile cover 501 can be designed in a simpler fashion, because the auxiliary instrument 507 is not guided from the rear through the drive unit.

Figure 20:
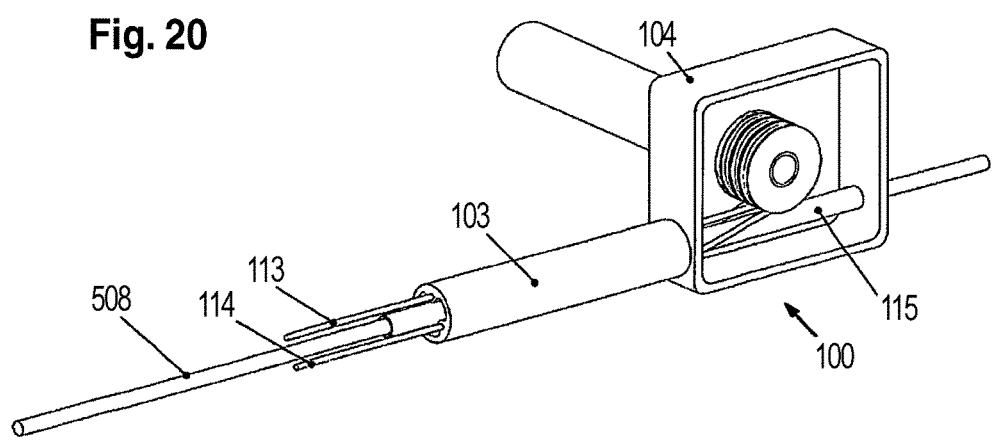
FIG. 20 a part of an instrument of an instrument assembly according to another embodiment of the present invention.

FIG. 20 shows a part of an instrument of an instrument assembly according to another embodiment of the present invention in which the axis of the drive and the axis of the shaft are orthogonal. Here, both stiff as well as flexible auxiliary instruments can be inserted and/or passed through. The auxiliary instrument 508 is fed from the rear through a guiding tube 115 and through the housing 104 to the distal end of the instrument shaft 103 and fixed. Subsequently, the auxiliary instrument 508 can be used like a common robot-guided instrument and moved with the degrees of freedom provided by the instrument 100 in the surgery area. Here, too, no design space is required at the proximal end of the instrument shaft in order to insert the auxiliary instrument 508.

The drive unit provides the mechanic drive capacity for all active degrees of freedom of the surgical instrument. It is located at the proximal end of the instrument and is designed as an independent module which is suitable to drive different instruments. In order to avoid any contamination of the surgery area the drive unit is hermetically sealed with a sterile protective cover.

The detachable instrument interface is located between the drive unit and the surgical instrument. Its primary purpose is the mechanical connection of the surgical instrument to the drive unit. On the one hand it provides a force flux between the drive and instrument functional units, and ensures a precise and repeatable relative positioning and fixation of these units. In order to transmit the required mechanical power to the instrument, the detachable instrument interface additionally comprises detachable couplings, which generate the force flux between the individual drives in the drive unit and the drive trains in the instrument. In order to ensure the sterility of the surgical instrument under all circumstances, the detachable instrument interface acts simultaneously as a sterile barrier between the unsterile drive unit and a sterile instrument.

Advantageously the coupling of a surgical instrument of an instrument assembly according to one embodiment of the present invention is simple and requires no detailed special professional knowledge in robotic systems. The detachable instrument interface according to one embodiment advantageously allows the repeatable and reliable coupling of the instrument including all force transmission elements without any visual inspection. The interface can preferably transmit one or more drive motions from a drive unit to a surgical instrument, while the sterility at the instrument side can be ensured. The drive unit and/or the detachable instrument interface advantageously require little structural space in order to minimize the risk of collision in case of a system with several robots, for example. In order to improve the performance of a robotic guided instrument with regards to control technology the transmission of mechanic drive energy to the surgical instrument shall be embodied with as little play and slippage as possible.

Figure 21A:
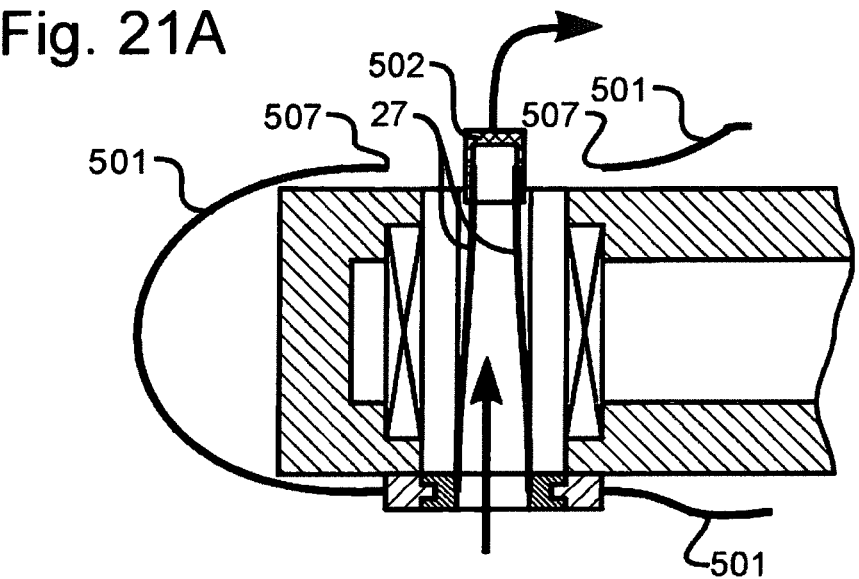
FIGS. 21A, 21B: an encompassing of a robot with a cover according to one embodiment of the present invention.
Figure 21B:
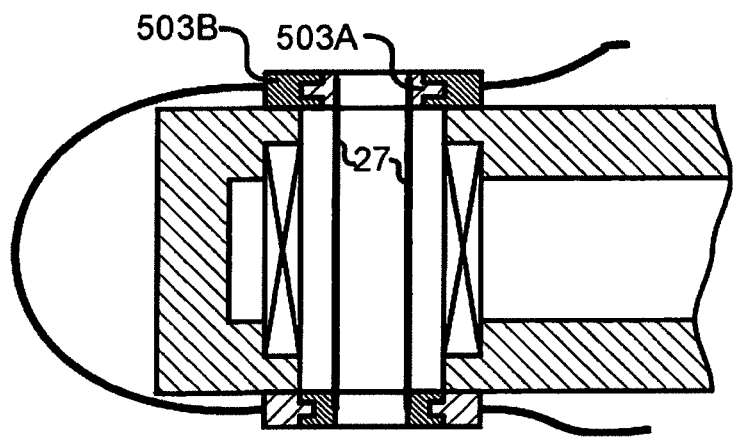

FIGS. 21A, 21B show an enclosure of a robot with a cover according to one embodiment of the present invention. The robot, with its robotic hand being partially indicated in FIGS. 21A, 21B comprises a hollow shaft. A tubular interior passage 27 of a cover 501 is guided through it, which includes an outlet opening 507. The end of the inner passage 27 guided through is covered at its beginning with a blind plug 502, for example in a clamped fashion, which has a closed face and a tubular jacket, in order to protect the interior and a facial circumferential section of the inner passage 27 from soiling when being guided through.

The blind plug 502 is guided through the hollow shaft and the outlet opening 507 (FIG. 21A) and subsequently removed. At the circumferential section of the inner passage 27, which was released thereby, and the edge of the outlet opening 507 a sterile cap ring 503A, 503B is fastened, once more for example in a clamping fashion (FIG. 21B). This way, in a simple fashion a sterile encompassing of the robot can be provided with the hollow shaft and/or simultaneously the drive unit of an instrument assembly.

In the exemplary embodiment the inner passage 27 is supported with its end (bottom in FIGS. 21A, 21B) opposite the blind plug 502 and/or the cap ring 503 at the cover 501 in a rotary fashion, for example as described above with reference to the intermediate elements of the instrument interface. The cap ring is embodied in two parts, with one part 503A of the cap ring, fastened at the circumferential section of the inner passage, being supported rotationally at a part 503B of the cap ring fastened at the outlet opening of the cover. This way, the inner passage 27 in its entirety is supported rotationally at the cover 501 and can be entrained, in particular with an auxiliary instrument moved by the hollow shaft. In a variant (not shown) the inner passage may also be embodied integrally and/or in one piece with the cover and/or connected thereto via a one-piece cap ring, with it being possible to compensate any potential rotation of the hollow shaft, for example by loose [sections] of the inner passage and/or the cover.

FIG. 22 shows a part of a minimally invasive surgical instrument according to one embodiment of the present invention in a longitudinal cross-section with an instrument module 1 and a detachable instrument part 2 connected thereto.

The instrument part comprises an instrument shaft 22 with an end effector (not shown), which can be inserted into a patient, with the instrument module comprising a drive for actuating the end effector, as well as an electro-mechanical interface for fastening at a robot (not shown).

The instrument module 1 comprises a coupling element assembly with several coupling elements in the form of translationally moved tappets 10, which are guided in a sliding bearing 12 of the instrument module in a torque-proof but displaceable fashion, and with only one being shown in FIG. 22 for better visibility. The instrument part comprises a respective counter element assembly with counter elements in the form of translationally moved (counter) tappets 20, which are guided in a sliding bearing of the instrument shaft 22 in a torque-proof but displaceable fashion in order to respectively actuate a degree of freedom of the end effector. The translational movement of the tappets and counter-tappets in order to actuate an intra-corporeal degree of freedom of the minimally invasive instrument by the extra-corporeal drive is indicated in FIG. 22 by the double arrow of the motion.

The tappets 10 of the coupling element assembly can be magnetically coupled with the counter-tappets 20 of the counter element assembly. For this purpose, the tappets 10 each include a magnetic assembly for a magnetic coupling of the opposite counter tappet 20, which has a section 21 which can be magnetically impinged, comprising a ferromagnetic or permanently magnetic material. The tappets 10 of the coupling element assembly include a magnetically conductive section 11 made from a ferromagnetic material, which has an exterior ring and a central yoke.

An electric coil is arranged about this yoke and cast with a non-magnetic casting material 13, in order to integrally form an electromagnet 31 of the magnetic assembly with the tappet 10, which can optionally be electrified and/or is electrified by a control means provided for this purpose, which is implemented in a drive control of the instrument (not shown).

Additionally, each magnetic assembly includes a permanent magnet 30, which is opposite the electromagnet 31, with its magnetic field being at least essentially compensated by the electrified electromagnet 31 in a facial coupling area of the tappet and the counter-tappet.

Via the optionally electrifiable electromagnet 31 a current-free closed coupling is provided between the coupling element and the counter element; as long as the electromagnet 31 is current-free, the permanent magnet 30 couples the section 21 of the counter tappet 20, which can be impinged magnetically, in a secure fashion to the magnetically conductive section 11 of the tappet 10. By electrifying the electromagnet 31 it compensates the magnetic field of the permanent magnet 30 in its facial coupling area to such an extent that the instrument part 2 can be removed from the drive module 1, preferably under its own weight and/or minor manual force.

Similarly, the electrified electromagnet 31 and the permanent magnet 30 may also act in the same direction and/or their magnetic fields may amplify each other in a facial coupling area of the tappet and the counter tappet.

Optionally a sterile barrier 40 is arranged between the coupling element assembly and the counter element assembly, which is embodied like a film and is flexible in the coupling area in order to follow under elastic deformation any translational movement of the tappet 10 and the counter tappet 20 in order to actuate the end effector.

In one variant, not shown, the permanent magnet 30 may be omitted in order to inversely provide a currentless open coupling between the coupling element and the counter element by an optional electrifying of the electromagnet 31; as long as the electromagnet 31 is electrified, it couples the section 21 of the counter tappet 20, which can be impinged magnetically, in a secure fashion to the magnetically conductive section 11 of the tappet 10. When the electromagnet 31 is currentless the instrument part 2 can be removed from the drive module 1.

FIG. 23 shows a part of a minimally invasive surgical instrument according to another embodiment of the present invention in an illustration according to FIG. 22. Equivalent elements are marked with identical reference characters so that reference is made to the other descriptions, and in the following only the differences from the embodiment shown in FIG. 22 are discussed.

In the embodiment of FIG. 23 the magnetic assembly is not provided with an electromagnet but only with the permanent magnet 30. In particular in order to decouple the coupling element from the counter element 10, 20 without rendering them distant from each other, in this embodiment the permanent magnet 30 can be displaced in the coupling element and/or the tappet 10 between the locked position shown in FIG. 23 and an unlocked position distanced therefrom indicated in dot-dash lines in FIG. 23, which is indicated in FIG. 23 by a dot-dash double arrow showing the motion. The permanent magnet 30 is guided in a displaceable fashion in a longitudinal bore of the tappet 10 and can be adjusted for example by an electromotive, hydraulic, pneumatic, and/or manual displacement of the thrust rod on which it is arranged, and locked in the locked and the unlocked position.

The facial, magnetically conductive section 11 of the tappet 10 is only magnetically impinged by the permanent magnet 30, at least essentially, when it is in the locked position. In the unlocked position (indicated in dot-dash lines in FIG. 23) the permanent magnet 30 is however separated from the magnetically conductive section 11 of the tappet 10 and arranged in a magnetically non-conductive section of the tappet 10 made from plastic with a permeability value $\mu_r$ which amounts to maximally 2.

By adjusting the permanent magnet 30 in the bore of the tappet 10 into the locked position, its magnetically conductive section 11 can be optionally impinged magnetically by the magnetic assembly to couple the counter tappet.

In the embodiment of FIG. 23 the optionally sterile barrier 40 comprises a stiff coupling part 41 made from a magnetically conductive material, in order to improve the mechanic force transmission and the magnetic coupling. In one variant, not shown, the optional sterile barrier may also be embodied like a film, as in FIG. 22, and/or the optional barrier may include a coupling part as the embodiment of FIG. 22.

In the embodiment of FIG. 23, a part comprising a non-magnetic material is marked 13. It may be designed as in the embodiment of FIG. 22 as a casting compound and thus it carries the same reference character. Similarly, the part 13 may be a molded part, which is fastened at the magnetically conductive section 11 and acts as a stop for the displaceable permanent magnet 30.

FIG. 24 shows a part of a minimally invasive surgical instrument according to another embodiment of the present invention in an illustration according to FIGS. 22, 23. Equivalent elements are again marked with identical reference characters so that reference is made to the other description, and in the following only the differences from the embodiment of FIGS. 22, 23 are discussed. In particular, the magnetic assembly and the magnetically conductive sections are not shown in FIG. 24 for a better overview, they may in particular be embodied as shown in FIG. 22 or 23 and/or explained with reference thereto.

In the embodiment of FIG. 24, in addition to the magnetic coupling the tappet 10 and the counter tappet 20 can be connected and/or are connected in a form-fitting fashion. For this purpose, the tappet 10 engages a sheath and/or socket section of the counter tappet 20 like a pin when the coupling element and the counter element are coupled to each other. This way the coupling element and the counter element are fixed in a form-fitting fashion perpendicular in reference to their vertical longitudinal extension, in FIG. 24, i.e. horizontal in the drawing level and/or perpendicular in reference thereto, with the magnetic coupling fixates them in a force-fitting fashion in the direction of their longitudinal extension.

The tappet 10 and the counter tappet 20 are thereby centered in reference to each other in a form-fitting fashion. In order to compensate a lateral and/or angular offset the counter tappet 20 is supported in the embodiment of FIG. 24 with play in the sliding bearing of the instrument shaft 22.

In the embodiment of FIG. 24 the magnetically conductive section 21 of the counter tappet 20 is arranged inside the sheath and/or socket section of the counter tappet 20 in order to this way preferably avoid any unintended magnetic interference.

In the embodiments explained, the coupling element and the counter element are formed like tappets and coupled to each other abutting and/or at their faces, with the magnetic assembly of the coupling element and the counter element pulling them towards each other in the direction of their longitudinal extension in order to transfer tensile forces, while pressures are transmitted in a form-fitting fashion.

Additionally or alternatively, coupling elements and counter elements 10, 20 can be rotationally mobile in the embodiments in order to respectively actuate a degree of freedom of the end effector. The magnetic assembly pulls the coupling element and the counter element in the direction of their longitudinal direction towards each other in order to allow a transmission of torque in one embodiment. This can occur in a friction-fitting fashion due to the axial tension by the magnetic assembly. Equivalently, it may also occur in a form-fitting fashion. For this purpose, in a variant not shown the tappet 10 or the counter tappet 20 may include one or more eccentric projections, in particular gears, which engage respective recesses, in particular inverse gears in the counter tappets 20 and/or the tappet 10, when the coupling element and the counter element are magnetically coupled to each other. In one variant, not shown either, the tappet 10 or the counter tappet 20 includes Hirth-gears.

In such a case, the coupling part 41 may in particular be connected via a rotary seal in a rotational fashion to the remaining barrier 40. Similarly the coupling part 41 can be connected via a translational seal to the remaining barrier 40 in a displaceable fashion, as respectively indicated in FIG. 24.

Figure 25:
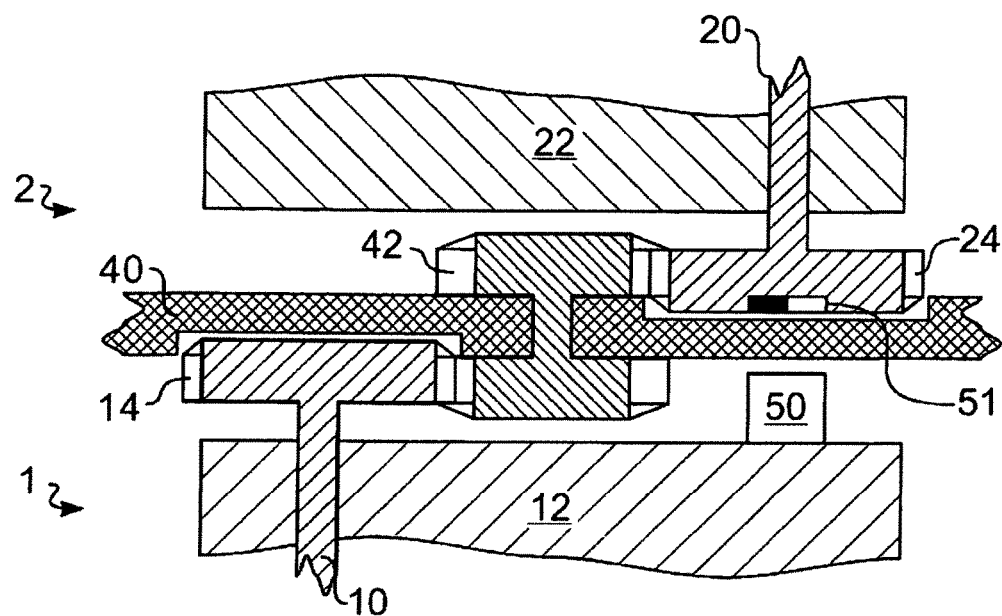
FIG. 25 a part of a surgical instrument according to another embodiment of the present invention.
Figure 26:
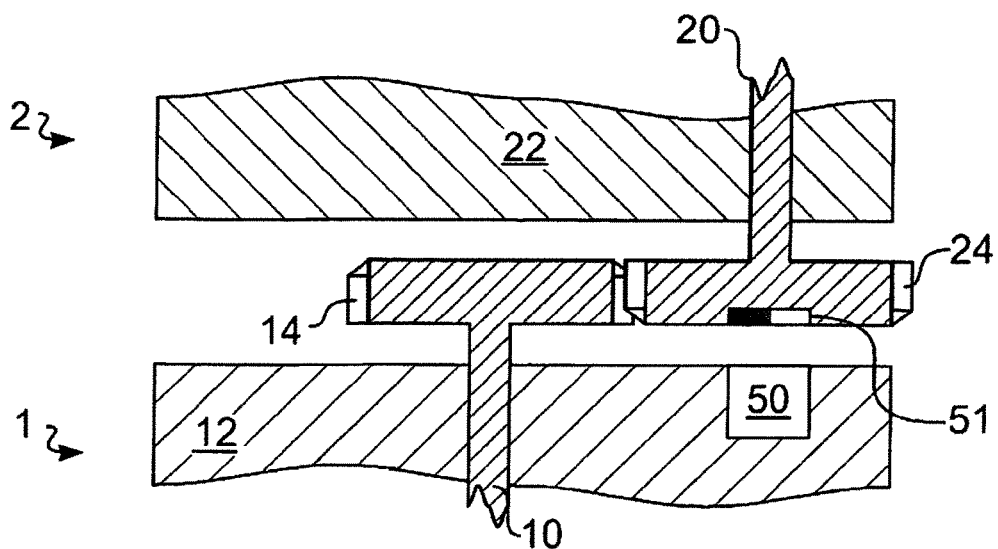
FIG. 26 a part of a surgical instrument according to another embodiment of the present invention shown to FIG. 4 in a respective illustration.

FIGS. 25, 26 respectively show a part of a minimally invasive surgical instrument according to another embodiment of the present invention in a longitudinal cross-section with an instrument module 1 and a detachable instrument part 2 connected thereto. Equivalent elements are once more marked with identical reference characters so that reference is made to the above-stated description, and in the following only the differences from the embodiment of FIGS. 22-24 are discussed.

In the embodiment of FIG. 26 a coupling element in the form of a rotationally supported drive shaft 10 of an electric motor of the drive (not shown) and a counter element in the form of a rotationally supported drive shaft 20, supported parallel and offset in reference thereto, of an effector of the instrument (not shown) can be coupled to each other in a form-fitting fashion by mutually engaging spur gears 14, 24. In the embodiment of FIG. 25 a sterile barrier 40 is arranged between the coupling assembly and the counter element assembly with a rotationally supported coupling part 42 having two spur gears, which engage the spur gears 14 and/or 24 and this way also couple the coupling element and the counter element 10, 20 in a form-fitting fashion.

A rotary bearing and/or a housing of the instrument module 1 and/or the instrument part 2 are indicated with 12 and/or 22 respectively.

In a variant, not shown, the coupling element and the counter element 10, 20 may additionally or alternatively be magnetically coupled to each other in a torque-proof fashion, as explained above with reference to FIGS. 22-24.

The spur gears between the spur wheels 14, 24 and perhaps 42 are ambivalent and/or can be coupled in various orientations, offset in reference to each other by the tooth pitch.

In order to nevertheless be able to actuate the end effector by a drive without any prior recalibration, the instrument module 1 includes in the embodiments of FIGS. 25, 26 a touchless angle sensor in the form of a magnetic encoder for detecting the angular position of the coupled drive shaft 20 in reference to the housing and/or the rotary bearing 12 of the instrument module 1. The drive shaft 20 comprises accordingly a torque-proof transmitter in the form of a permanent bar magnet 51, which is embodied to be detected by the angle sensor 50. The north-south axis of the bar magnet 51 is aligned perpendicular in reference to the axis of rotation of the drive shaft 20.

During or after the coupling of the instrument part 2 to the instrument module 1 in one or more alignments, the angular position of the transmitter 51 is detected in the coupled drive shaft 20, which in FIGS. 25, 26 once more is only shown as an example, in reference to a point fixed at the housing of the instrument module by the angle sensor 50 of the instrument module. This way, after the detection of the orientation of the counter elements, a position of the end effector is also known, so that the end effector can be correctly actuated by a drive without recalibration.

While the present invention has been illustrated by a description of various embodiments, and while these embodiments have been described in considerable detail, it is not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit and scope of the general inventive concept.

LIST OF REFERENCE CHARACTERS

In the FIGS. 1 to 21:
1, 100, 101, 400 Instrument
2, 102 Drive unit
4 Connection flange
3, 103, 505 Instrument shaft
5, 105, 501 (Sterile) cover
6, 104 Housing
7, 8, 9 Electric motor
11, 12, 14, 28, 29, 30 Bearing site
19, 20, 21, 206, 207, 208 Intermediate element 22 Transmission
23, 24, 25, 37, 38, 200, 201, 202, Sliding sheath (guide bar) 406, 407
26, 39, 40 Tensile/thrust means
31-36, 200-205, 300-305 Spur gearing (coupling part)
27, 115 (Sterile) guide tube
37 Helical groove
38 Pin
41, 42, 43 Groove guide
10, 13, 15, 16, 17, 18, Drive shaft 106, 107, 108, 109, 110, 111, 404, 405, 406
402 Instrument kinetics
403 End effector
408, 409 Coupling rod
100 Transmission at the instrument side
112, 113, 114 Pulleys
115 Guide tube
116, 117, 118 Intermediate coupling segment
209, 210, 211 Fastening ring
500 Instrument interface
501 (Sterile) film cover
502 Blind plug
503 Cap ring
504, 507, 508 Auxiliary instrument
506 Tubular section
507 Outlet opening
In the FIGS. 22 to 26:
1 Instrument module
10 Tappet; shaft (coupling element)
11 Magnetically conducting section
12 Housing of the instrument module, sliding/rotary bearing
13 Casting compound, form part/component
14 Spur wheel
2 Instrument part
20 Tappet, shaft (counter element)
21 Section that can be magnetically impinged
22 Instrument shaft, sliding/rotary bearing
24 Spur wheel
30 Permanent magnet
31 Electromagnet
40 Sterile barrier
41, 42 Coupling part
50 Angle sensor
51 Permanent bar magnet (transmitter)

What is claimed is:

1. An instrument assembly for detachable fastening at the robot of a robotic surgery system, the instrument assembly comprising:
    a drive unit comprising at least one rotary drive motor with a drive shaft;
    an instrument detachably connected to the drive unit, the instrument including an instrument shaft and at least one drive shaft;
    the drive shaft of the drive unit and the drive shaft of the instrument each including a coupling part cooperating to couple the drive shaft of the drive unit to the drive shaft of the instrument such that drive moments caused by rotation of the drive shaft of the drive unit about its own longitudinal axis are transmitted to the drive shaft of the instrument for rotation about its own longitudinal axis, which drive moments actuate an end effector located at a distal end of the drive shaft of the instrument; and
    an instrument interface arranged between the drive unit and the instrument.

2. An instrument assembly according to claim 1, wherein the coupling part of the drive shaft of the drive unit and the coupling part of the drive shaft of the instrument are magnetically coupled to each other.

3. The instrument assembly of claim 1, further comprising at least one of:
    an auxiliary instrument; or
    a drive for actuating an end effector;
    wherein the auxiliary instrument or the drive is detachably inserted through the instrument of the instrument assembly.

4. The instrument assembly of claim 1, wherein at least one drive shaft of the drive unit and one drive shaft of the instrument are arranged coaxially.

5. The instrument assembly of claim 1, wherein the drive unit comprises at least one inner drive shaft concentrically arranged in an outer hollow drive shaft.

6. The instrument assembly of claim 5, wherein the inner drive shaft is a hollow drive shaft.

7. The instrument assembly of claim 1, wherein the rotary drive motor of the drive unit is at least one of:
    coaxially aligned with its drive shaft;
    arranged parallel offset relative to its drive shaft; or
    arranged angularly relative to its drive shaft.

8. The instrument assembly of claim 1, wherein the coupling part of the drive unit drive shaft is axially displaceable in a direction along the drive shaft.

9. The instrument assembly of claim 8, wherein the coupling part is biased in a direction along the drive shaft.

10. The instrument assembly of claim 1, wherein the instrument comprises at least one inner drive shaft arranged concentrically within an outer hollow drive shaft.

11. The instrument assembly of claim 10, wherein the inner drive shaft of the instrument is a hollow drive shaft.

12. The instrument assembly of claim 1, wherein the instrument drive shaft is one of:
    coaxially arranged relative to the instrument shaft;
    arranged parallel offset relative to the instrument shaft; or
    angularly arranged relative to the instrument shaft.

13. The instrument assembly of claim 1, further comprising a transmission for converting a rotation of the drive unit drive shaft or the instrument drive shaft into a translation of at least one of a tensile means or a thrust means;
    wherein at least one of:
        the transmission comprises a guide bar, or
        the transmission is arranged in one half of the instrument shaft and either faces the drive unit or faces away from the drive unit.

14. The instrument assembly of claim 1, wherein the drive shaft of the instrument is a hollow drive shaft.

15. The instrument assembly of claim 1, wherein the drive shaft of the drive unit is a hollow drive shaft.

16. A robotic surgery system comprising a robot and an instrument assembly in accordance with claim 1 detachably fastened at the robot.

17. An instrument assembly for detachable fastening at the robot of a robotic surgery system, the instrument assembly comprising:
    a drive unit comprising at least one rotary drive motor with a drive shaft;
    an instrument detachably connected to the drive unit, the instrument including an instrument shaft and at least one drive shaft;
    the drive shaft of the drive unit and the drive shaft of the instrument each including a coupling part cooperating to couple the drive shaft of the drive unit to the drive shaft of the instrument; and
    an instrument interface arranged between the drive unit and the instrument;

wherein the drive shaft of the drive unit is hollow, the instrument assembly further comprising:

a cover having a tubular conduit adapted to be passed through the hollow shaft of the drive unit and through an outlet opening of the cover;

wherein the tubular conduit includes a blind plug and a cap ring for fastening at an outer circumferential section of the tubular conduit; and wherein the outer circumferential section of the tubular conduit is made accessible by removing the blind plug.

18. A method for enclosing a robot or a drive unit for an instrument assembly with a cover, the method comprising:

obtaining an instrument assembly for detachable fastening at the robot of a robotic surgery system, the instrument assembly comprising:

a drive unit comprising at least one rotary drive motor with a drive shaft, an instrument detachably connected to the drive unit, the instrument including an instrument shaft and at least one drive shaft, the drive shaft of the drive unit and the drive shaft of the instrument each including a coupling part cooperating to couple the drive shaft of the drive unit to the drive shaft of the instrument, and an instrument interface arranged between the drive unit and the instrument;

obtaining a cover having a tubular conduit adapted to be passed through the hollow shaft of the drive unit and through an outlet opening of the cover;

guiding a blind plug through the hollow shaft and the outlet opening of the cover;

removing the blind plug to uncover an outer circumferential section of the tubular conduit; and fastening a cap ring at the outer circumferential section of the tubular conduit.

* * * * *